US010175154B2

(12) United States Patent
Campbell

(10) Patent No.: US 10,175,154 B2
(45) Date of Patent: Jan. 8, 2019

(54) METHODS AND SYSTEM FOR SLIDE PROCESSING

(71) Applicant: William Eugene Campbell, Marietta, GA (US)

(72) Inventor: William Eugene Campbell, Marietta, GA (US)

(\*) Notice: Subject to any disclaimer, the term of this patent is extended or adjusted under 35 U.S.C. 154(b) by 167 days.

(21) Appl. No.: 15/112,310

(22) PCT Filed: Jan. 17, 2015

(86) PCT No.: PCT/US2015/011879
§ 371 (c)(1),
(2) Date: Jul. 18, 2016

(87) PCT Pub. No.: WO2015/109270
PCT Pub. Date: Jul. 23, 2015

(65) Prior Publication Data
US 2016/0370264 A1    Dec. 22, 2016

Related U.S. Application Data

(60) Provisional application No. 61/928,566, filed on Jan. 17, 2014, provisional application No. 62/061,015, (Continued)

(51) Int. Cl.
*G01N 1/31* (2006.01)
*G01N 1/30* (2006.01)
(Continued)

(52) U.S. Cl.
CPC .......... *G01N 1/312* (2013.01); *G01N 1/2813* (2013.01); *G01N 1/30* (2013.01); *G01N 1/31* (2013.01);
(Continued)

(58) Field of Classification Search
CPC ............ G01N 1/30; G01N 1/31; G01N 1/312; G01N 1/2813; G01N 2001/317; G02B 21/34; B01L 9/52
See application file for complete search history.

(56) References Cited

U.S. PATENT DOCUMENTS 2,434,003 A    1/1948 Morrison
5,650,332 A *  7/1997 Gao ..................... G01N 1/2813
427/2.11
(Continued)

FOREIGN PATENT DOCUMENTS

WO    95/20176    7/1995

OTHER PUBLICATIONS

Supplementary European Search Report for related European Application No. 15737215.2, dated Aug. 14, 2017.
(Continued)

*Primary Examiner* — Benjamin R Whatley
(74) *Attorney, Agent, or Firm* — Thomas Horstemeyer, LLP

(57) ABSTRACT

Various examples of systems and methods are provided for slide processing. In one example, among others, a system for processing microscope slides includes a slide positioner that can adjust a position of a slide and a slide treatment system that can dispense a micro stream of a fluid at a location on the slide when the slide is positioned beneath a jet nozzle of the slide treatment system. The system can include a slide sled that can align a smearing slide with a surface of the slide including a fluid sample is disposed, and support the smearing slide at a predefined angle with respect to the surface of the slide. In another example, a method includes obtaining a slide including a sample disposed on a surface, positioning the slide below to a jet nozzle, and dispensing a micro stream of a fluid onto the sample using the jet nozzle.

21 Claims, 33 Drawing Sheets

Related U.S. Application Data filed on Oct. 7, 2014, provisional application No. 62/089,084, filed on Dec. 8, 2014.

(51) Int. Cl.
| | |
|---|---|
| *G01N 1/28* | (2006.01) |
| *G02B 21/34* | (2006.01) |
| *B01L 9/00* | (2006.01) |
| *H04L 12/02* | (2006.01) |
| *H04W 4/80* | (2018.01) |

(52) U.S. Cl.
CPC .......... *B01L 9/52* (2013.01); *G01N 2001/317* (2013.01); *G02B 21/34* (2013.01); *H04L 12/02* (2013.01); *H04W 4/80* (2018.02)

(56) References Cited

U.S. PATENT DOCUMENTS

| | | |
|---|---|---|
| 5,854,075 A | 12/1998 | Levine et al. |
| 2002/0037359 A1 | 3/2002 | Mutz et al. |
| 2003/0081209 A1* | 5/2003 | Takahashi .............. G01N 1/312 356/338 |
| 2005/0212837 A1 | 9/2005 | Nakagawa et al. |
| 2005/0250211 A1 | 11/2005 | Reinhardt et al. |
| 2007/0148046 A1* | 6/2007 | Nakaya ................... G01N 1/31 422/82.05 |
| 2009/0111101 A1 | 4/2009 | Tafas et al. |
| 2013/0162802 A1 | 6/2013 | Soenksen |
| 2013/0167770 A1 | 7/2013 | Shoffner et al. |

OTHER PUBLICATIONS

Response to Office Action from Foreign Associate to the European Patent Office dated Mar. 16, 2018 (responding to OA dated Sep. 7, 2017).

International Search Report for PCT/US15/11879 dated Apr. 13, 2015.

Australian Examination Report for application No. 2015206277 dated Nov. 7, 2018.

* cited by examiner

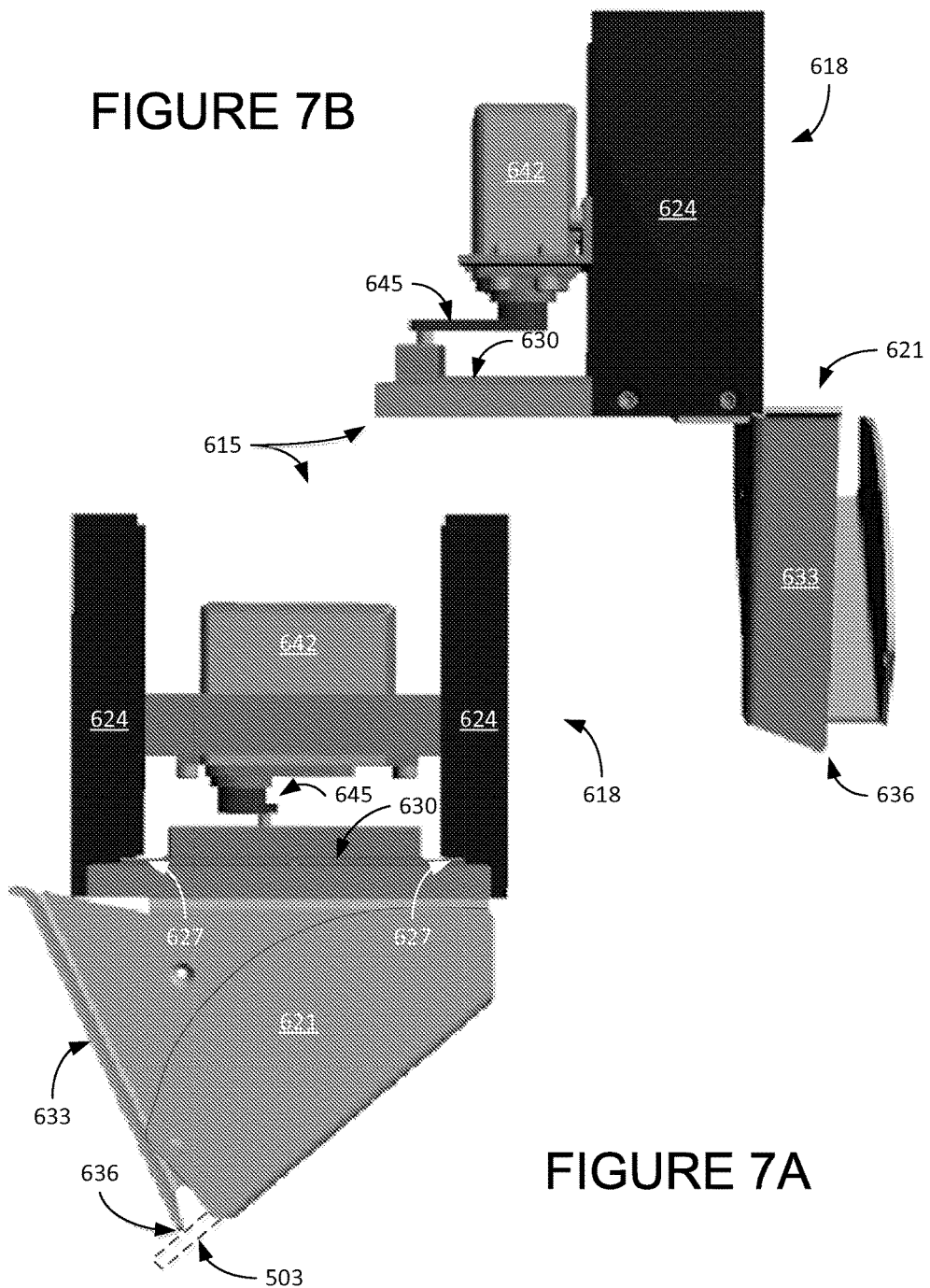

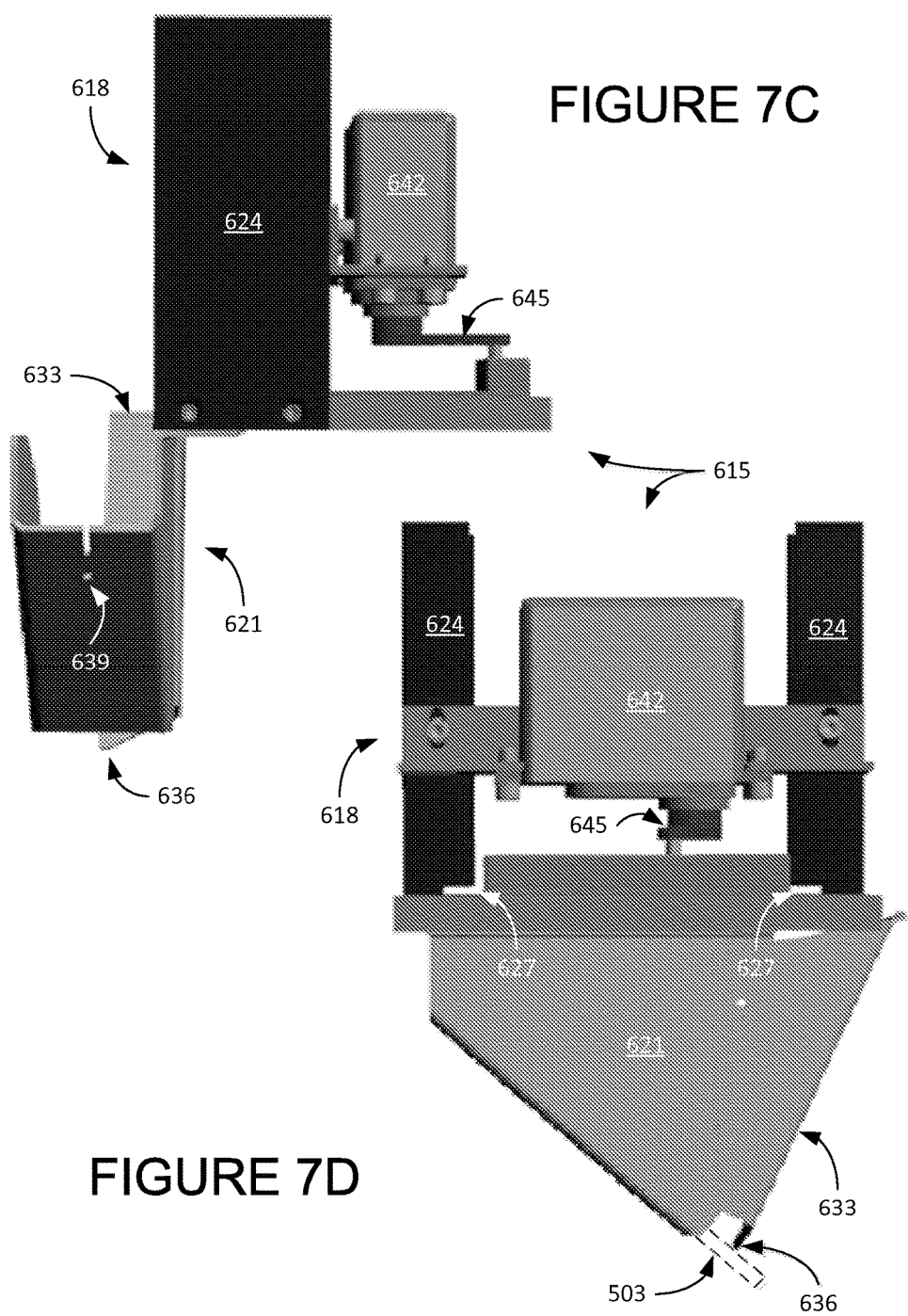

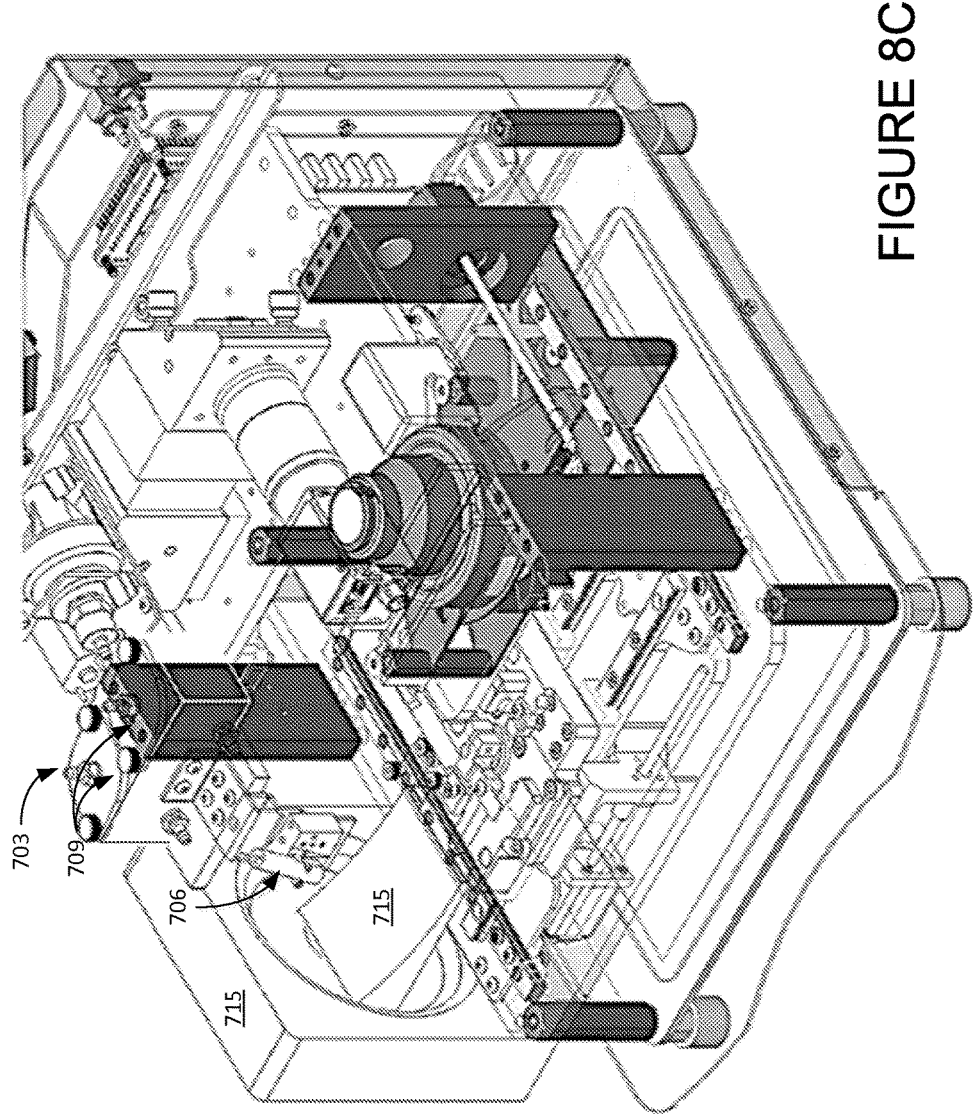

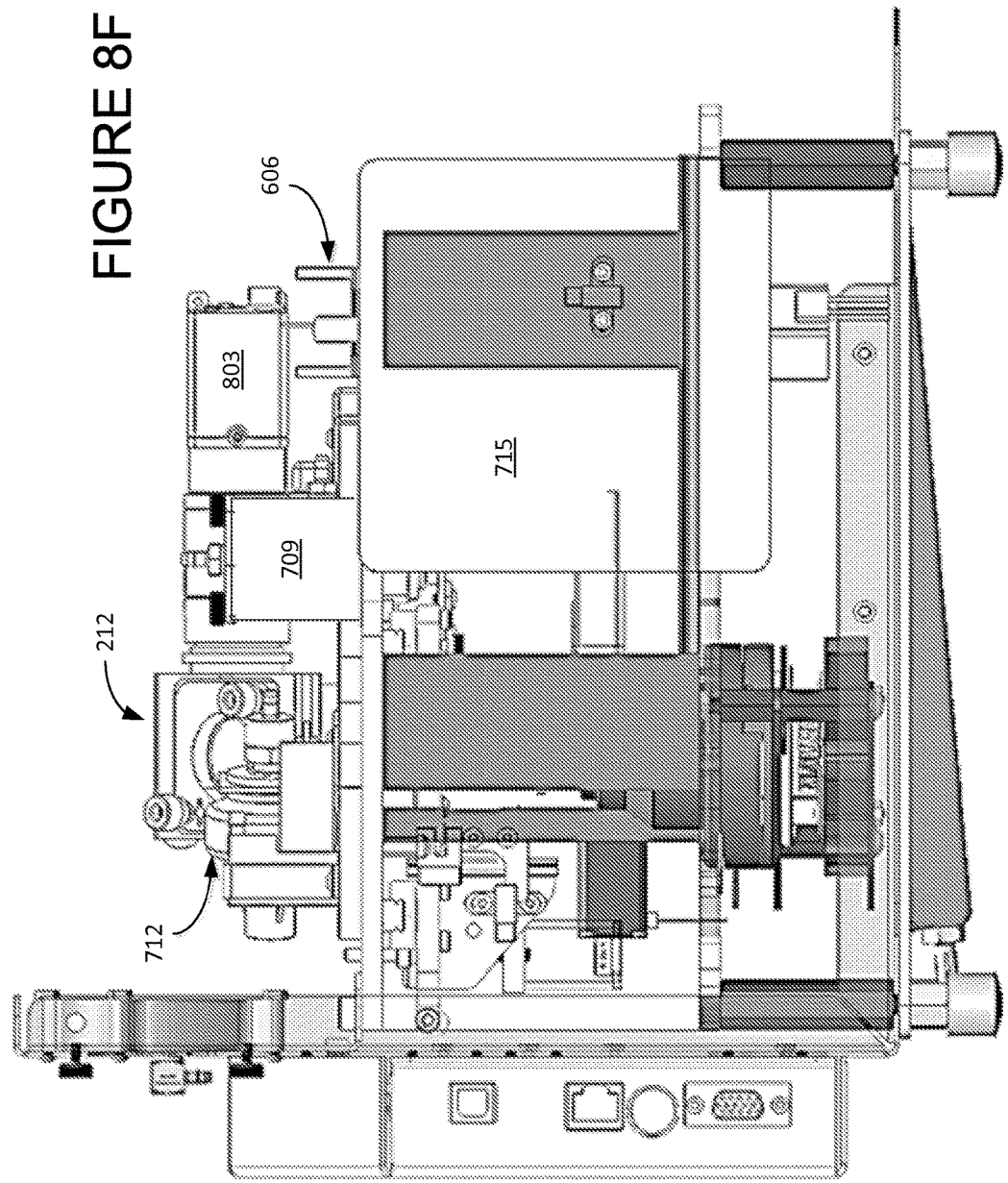

METHODS AND SYSTEM FOR SLIDE PROCESSING

CROSS REFERENCE TO RELATED APPLICATIONS

This application is the 35 U.S.C. § 371 national stage application of PCT Application No. PCT/US2015/011879, filed Jan. 17, 2015, which claims priority to, and the benefit of, co-pending U.S. provisional application entitled "METHODS AND SYSTEMS FOR SLIDE PROCESSING" having Ser. No. 61/928,566, filed Jan. 17, 2014; U.S. provisional application entitled "METHODS AND SYSTEMS FOR SLIDE PROCESSING" having Ser. No. 62/061,015, filed Oct. 7, 2014; and U.S. provisional application entitled "METHODS AND SYSTEMS FOR SLIDE PROCESSING" having Ser. No. 62/089,084, filed Dec. 8, 2014, all of which are hereby incorporated by reference in their entirety.

BACKGROUND

Microscope slides are prepared by hand for examination under a microscope. After a sample has been transferred to the slide and dried, the sample can be stained using a pipet or a bath to aid in examination. Such processing can be labor intensive, After drying, the slide is positioned under a microscope for examination and evaluation. In some cases, the processed slide is physically shipped to another facility for examination and evaluation.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 7A-7H include various views of an example of a slide dispenser used in the slide processing unit of FIGS, 1 through 5D in accordance with various embodiments of the present disclosure.

FIGS. 8A-8D and 8E-8F are perspective and side views (respectively) of an example of the interior of the slide processing unit of FIGS. 1 and 2 including a slide treatment system in accordance with various embodiments of the present disclosure.

DETAILED DESCRIPTION

Figure 1:
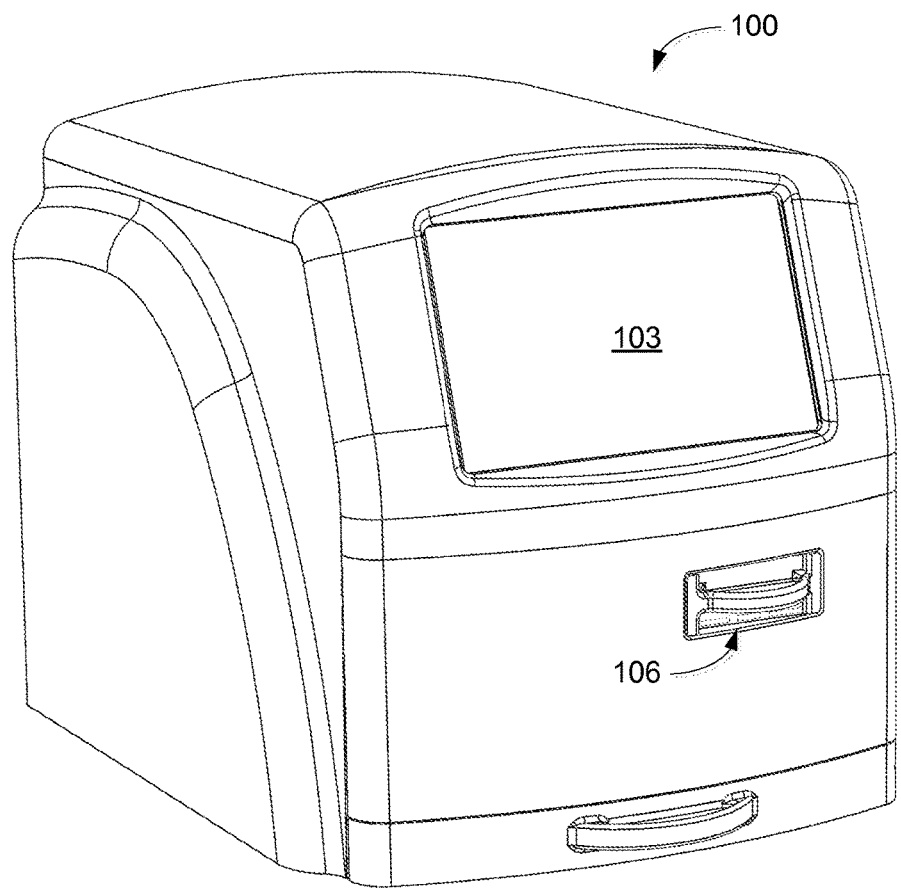
FIG. 1 is a drawing of an example of a slide processing unit in accordance with various embodiments of the present disclosure.

Disclosed herein are various examples of methods and systems related to microscope slide processing. Reference will now be made in detail to the description of the embodiments as illustrated in the drawings, wherein like reference numbers indicate like parts throughout the several views.

Slide processing units can be used for automated processing and imaging samples on a slide. Samples can include fluids (e.g., blood or other bodily fluids), tissue or other types of samples. Once transferred to a slide, the sample can be processed and imaged for examination by a user. Images of the sample can be captured with a camera and displayed and/or stored for examination by the user. The images of the slide can be locally and/or remotely accessed by the user in real time, or can be accessed by the user after capture and storage. For example, images of the processed sample can be stored in memory and subsequently accessed by the user when his or her schedule allows.

Referring to FIG. 1, shown is a perspective view of an example of a slide processing unit (or slide processor) 100, in accordance with various embodiments of the present disclosure. The slide processing unit 100 includes a display screen 103 for displaying and/or accessing information about the slide processing unit 100. For example, the processing status of a slide (e.g., staining, drying, imaging, etc.) can be indicated on the display screen 103. After the slide has been processed, an image of the sample can be provided through the display screen 103. In some implementations, the image of the sample can be manipulated through the display screen 103. The display screen 103 can be touch-sensitive to allow for user input through the display screen 103. In other embodiments, a user interface unit (e.g., keyboard, mouse, touch pad, etc.) can be communicatively coupled to the slide processing unit 100 through a communications interface The connection can be through a wireless link (e.g., WiFi, Bluetooth®, Kleer, Infrared, etc.) or through a wired connection.

Processing of the slide can be carried out in an enclosed environment to reduce the chance of contamination. A carriage 106 allows a user to insert a slide into the slide processing unit 100 for processing. With the carriage 106 pulled out of the slide processing unit 100, a slide including a sample can be inserted into the carriage 106. A guide or slot in the bottom of the carriage 106 can be used to hold the slide in the proper orientation for acquisition by a slide positioner that repositions the slide for processing and imaging within the slide processing unit 100.

Figure 2:
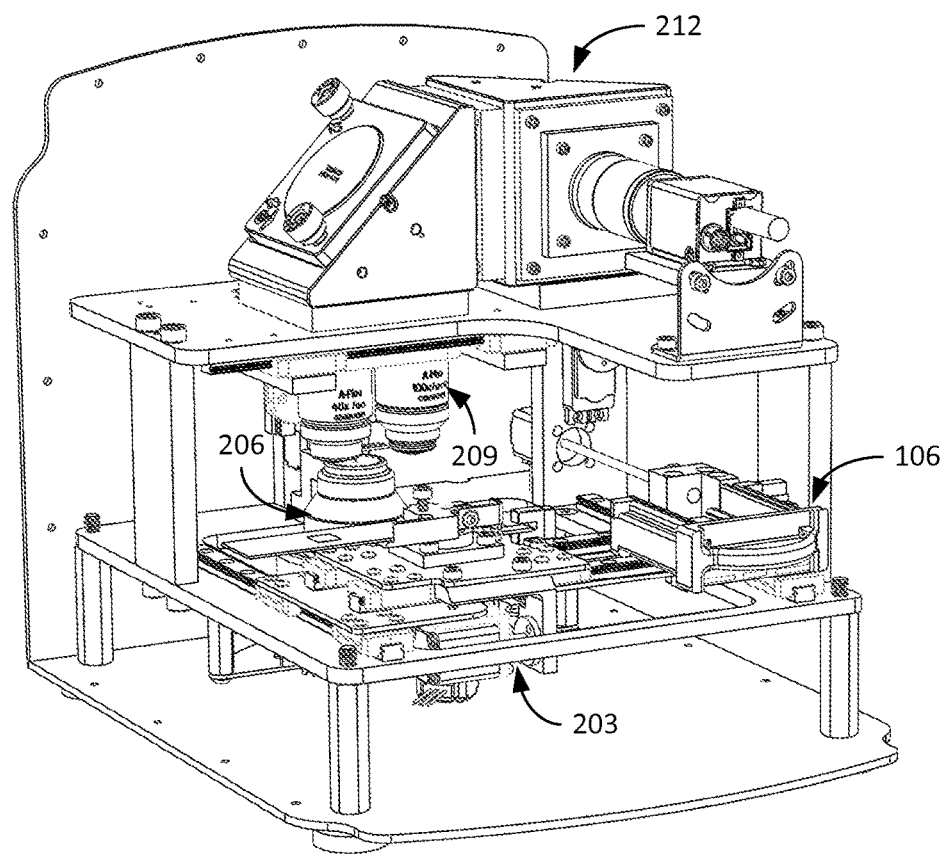
FIG. 2 is a perspective view of an example of the interior of the slide processing unit of FIG. 1 in accordance with various embodiments of the present disclosure.
Figure 3A:
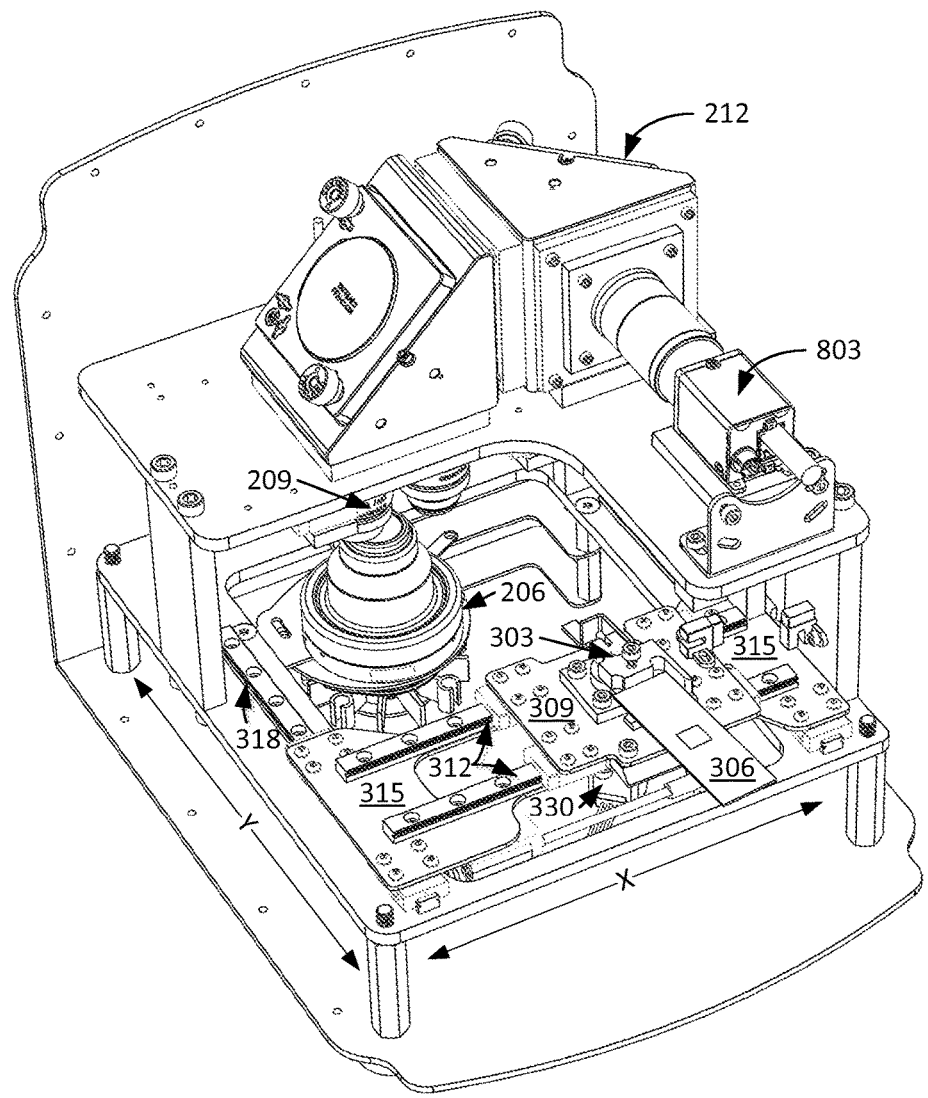
FIGS. 3A-3D are perspective views of the interior of the slide processing unit of FIG. 2 illustrating positioning of a slide in accordance with various embodiments of the present disclosure.

Referring next to FIGS. 2 and 3A-3D, show various perspective views of an example of a portion of the interior of the slide processing unit 100 with the cover including the display screen 103 removed. As shown in FIG. 2, the slide processing unit 100 includes a slide positioner 203, a light source 206, one or more microscopic lenses 209 and an image capture unit 212. The structure and operation of the slide positioner 203 is further illustrated in FIGS. 3A-3D. As seen in FIG. 3A, the slide positioner 203 includes a slide clamp 303 that grips the slide 306 when inserted through the carriage 106. The slide clamp 303 is supported by a mounting plate 309 that can be positioned along the x-axis and y-axis using guide rails and stepper or servo motors with finely pitched jack screws (with a high number of threads per inch). A first pair of guide rails 312 support the mounting plate 309 and allow for its movement along the x-axis. The guide rails 12 are secured in position by end plates 315 that are supported by a second pair of guide rails 318. The second pair of guide rails 318 allows movement of the first pair of guide rails 312, and thus the mounting plate 309 and slide clamp 303, along the y-axis.

Figure 3B:
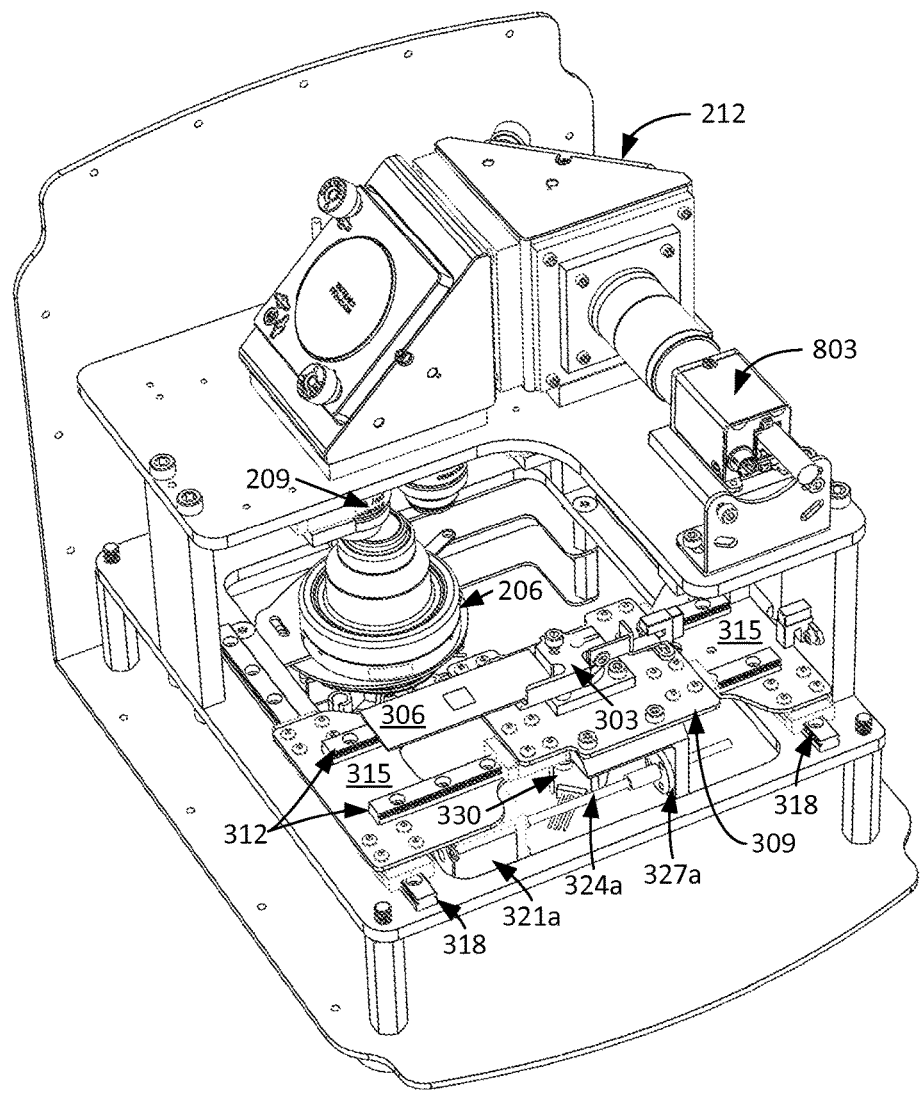
Figure 3C:
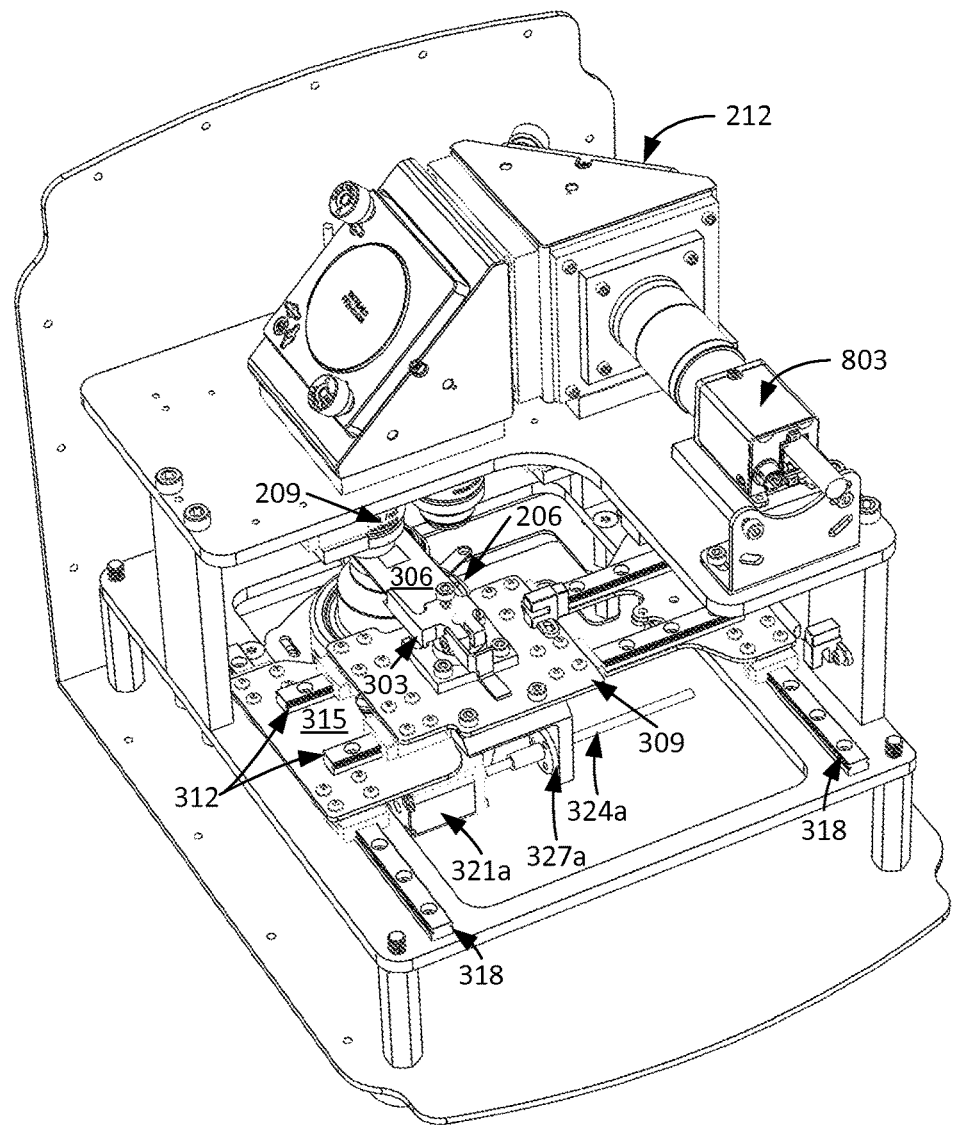

As can be seen in FIGS. 3B and 3C, a stepper or servo motor 321a can be mounted to one of the end plates 315 to control movement along the first pair of guide rails 312. The treads of the jack screw 324a can engage with a threaded portion of a bracket 327a (e,g., a threaded sleeve mounted to the bracket or a threaded opening through the bracket) secured to the mounting plate 309 such that rotation of the jack screw 324a moves the mounting plate 309 along the first pair of guide rails 312. Another stepper or servo motor 321b can be mounted (e.g., to a support structure) to control movement of the assembly including the slide clamp 303, mounting plate 309, first pair of guide rails 312 and end plates 315 along the second pair of guide rails 18 as illustrated in the cutaway view of FIG. 3D. The treads of the jack screw 324b can engage with a threaded portion of a bracket 327b (e.g., a threaded sleeve mounted to the bracket or a threaded opening through the bracket) secured to one of the end plates 315. Rotation of the jack screw 324b moves the assembly along the first pair of guide rails 312.

Figure 3D:
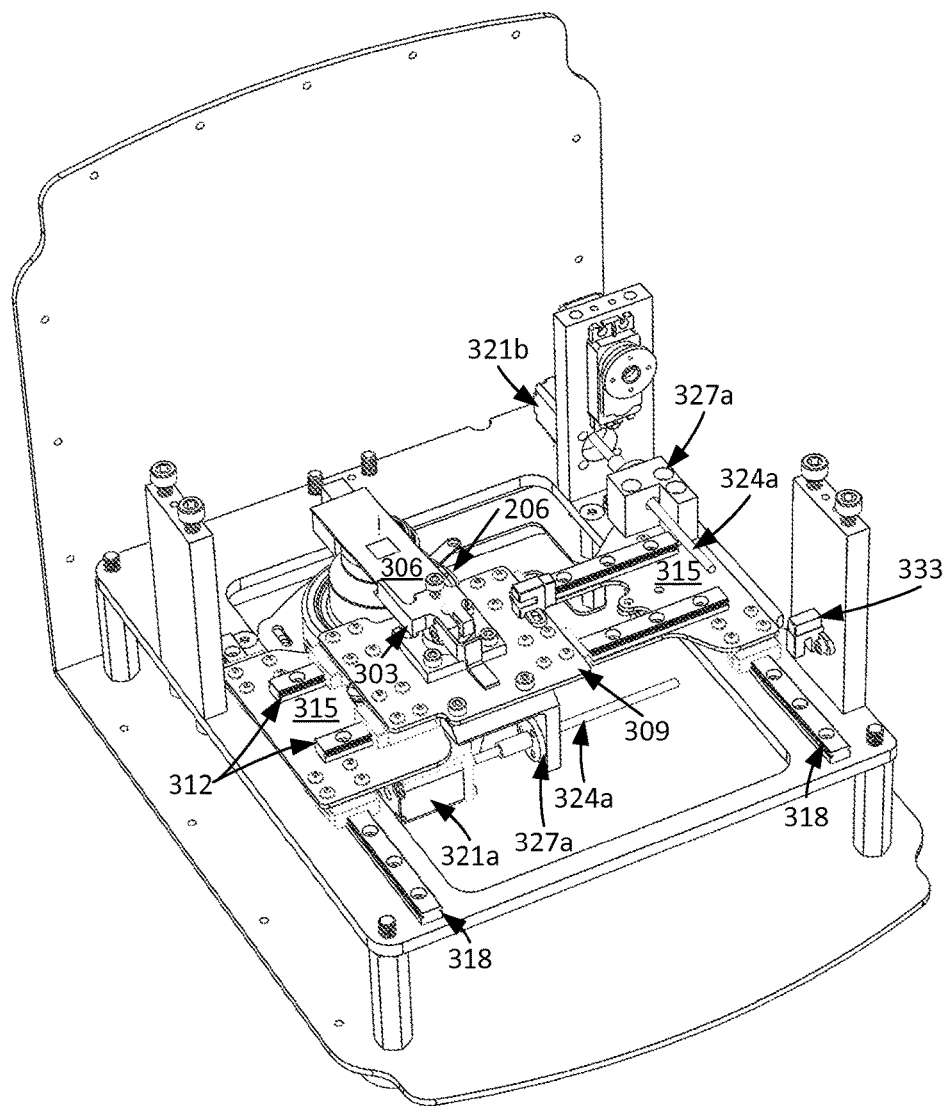

A low wear, low friction material such as a layer of polymer (e.g., polytetrafluoroethylene (PTFE), fluorinated ethylene propylene, etc.) or other appropriate material can be used to provide for smooth movement of the mounting plate 309 across the first pair of guide rails 312 and/or the end plates 315 across the second pair of guide rails 318. The position of the slide positioner 203 can be detected using one or more sensors. For example, a sensor 333 (e.g., a capacitive sensor, a magnetic sensor, an infrared sensor, a photosensitive sensor, etc.) can be used to detect the position of an end plate 315 when it reaches a travel limit along the second pair of guide rails 318 as illustrated in FIG. 3D. Similar sensors can be used to detect the position of the mounting plate 309 as it reaches a travel limit along the first pair of guide rails 312. These sensors can also be used as reference points for calibration and/or control of the slide positioner 203.

Figure 4A:
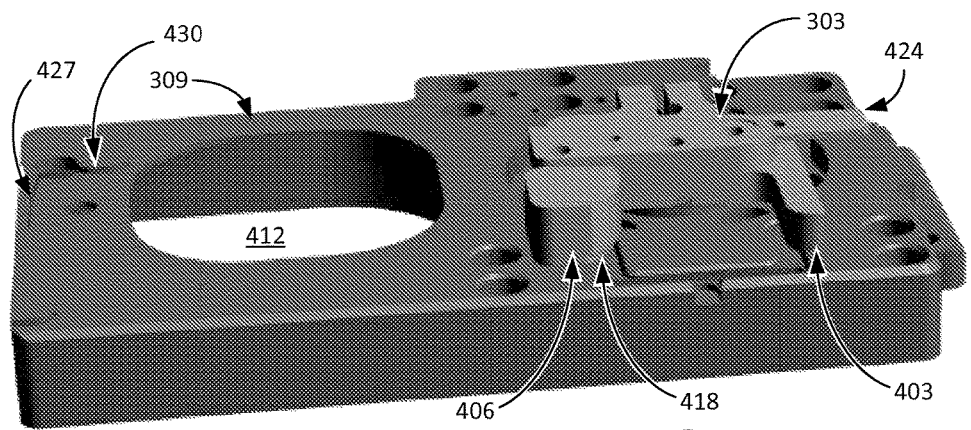
FIGS. 4A-4F are perspective views of an example of a mounting plate and slide clamp that can be used in the slide processing unit of FIGS. 1 and 2 in accordance with various embodiments of the present disclosure.
Figure 4B:
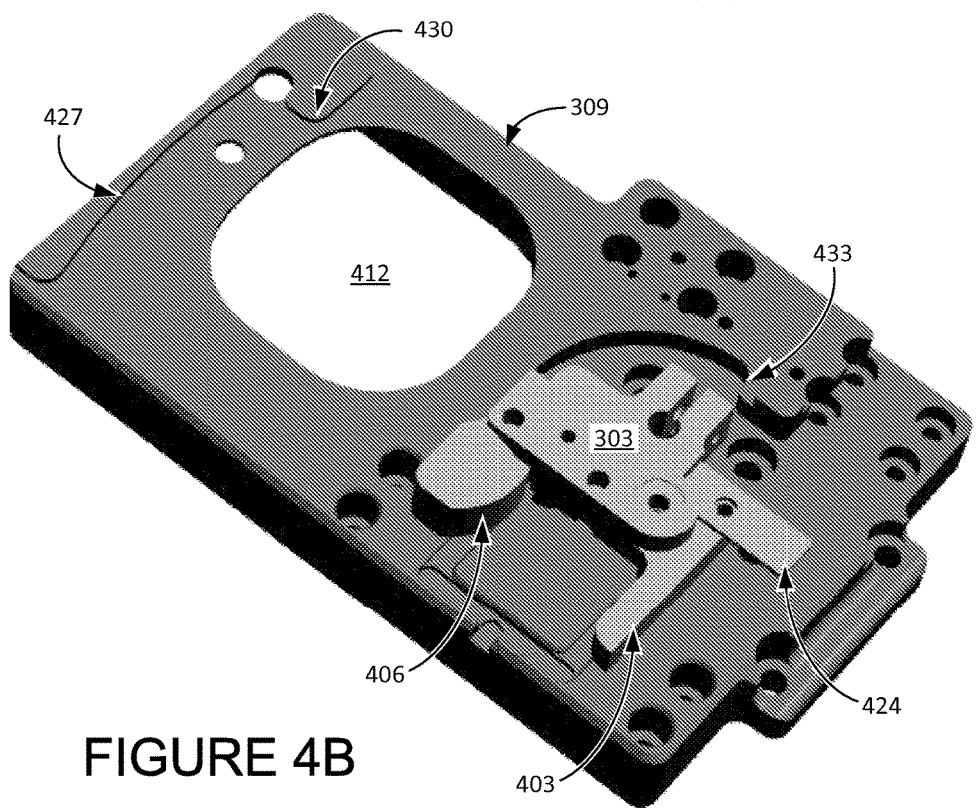
Figure 4C:
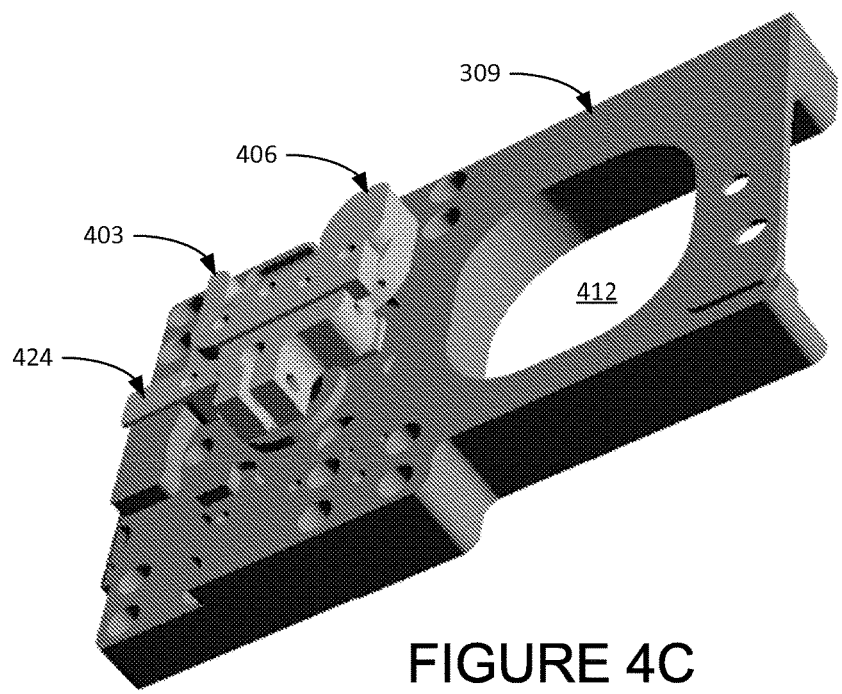
Figure 4D:
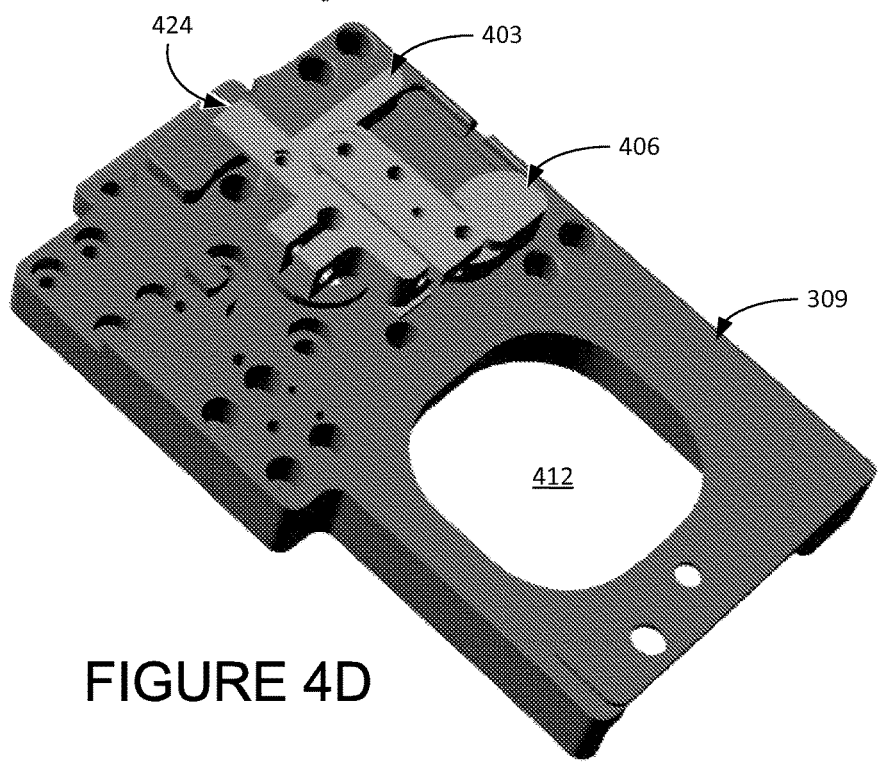
Figure 4E:
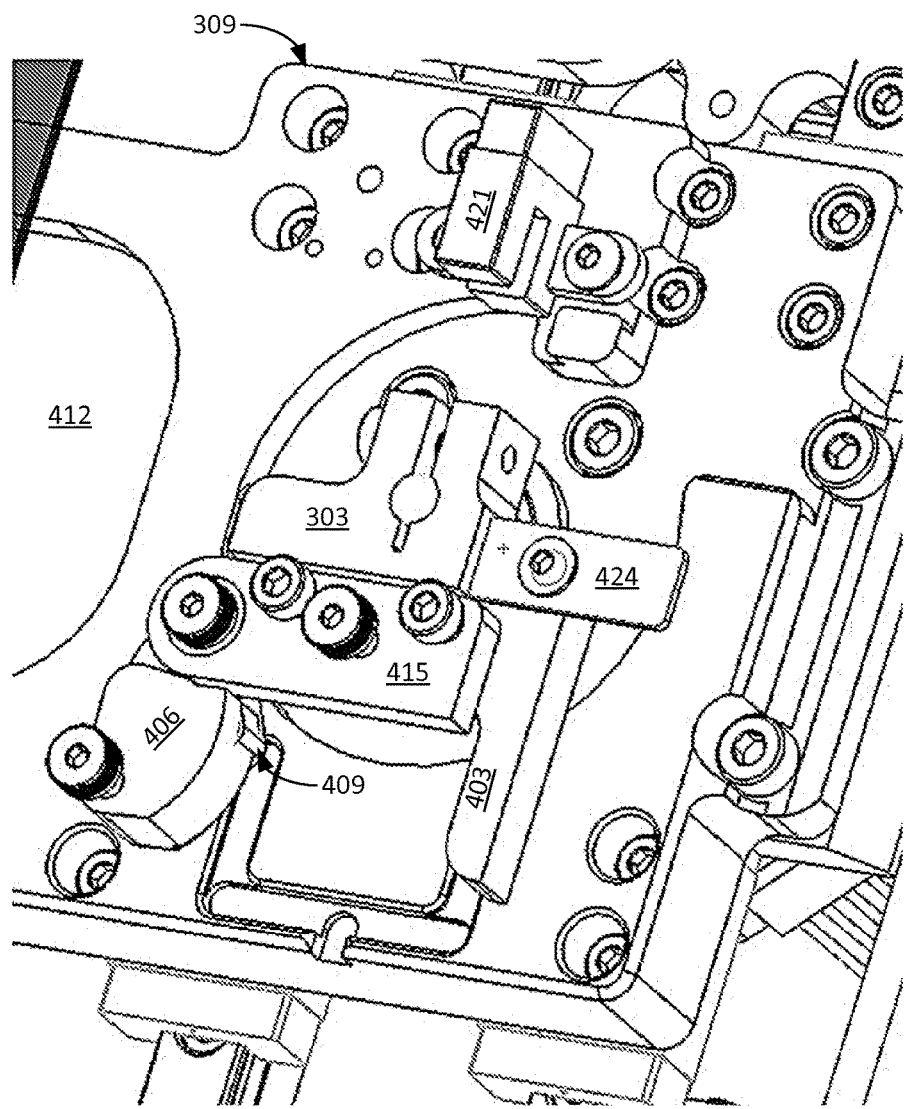
Figure 4F:
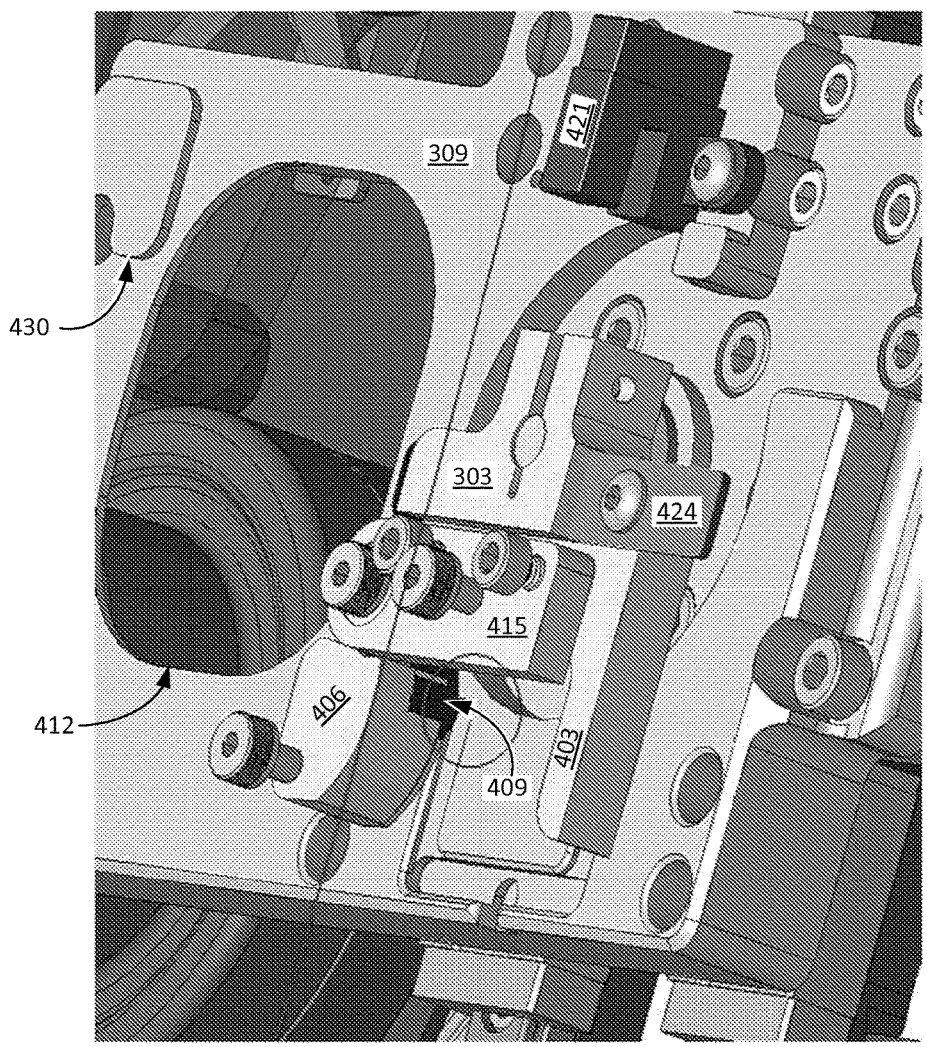

Referring to FIGS. 4A-4G, shown are various perspective views of a rotator assembly including the slide clamp 303 and mounting plate 309. A stepper or servo motor 330 can be mounted to a lower side of the mounting plate 309 as illustrated in FIGS. 3A and 38. The shaft of the stepper or servo motor 330 can extend through the mounting plate 309. With the slide clamp 303 secured to the shaft of the motor 330, the motor 330 can be used to control rotation of a e slide clamp 303 about the z-axis defined by the motor shaft. The slide clamp 303 includes an alignment arm 403 on a first side and a clamping arm 406 on a second side. The sample slide 306 can be inserted between the two arms 403 and 406. The alignment arm 403 is fixed in position to align one side of the slide, while the clamping arm 406 applies pressure to the opposite side the sample slide 306 to hold it in position against the alignment arm 403 during processing by the slide processing unit 100. A spring can be used to apply a clamping force with the clamping arm 406. As illustrated in FIGS. 4E and 4F, the clamping arm 406 can include a textured edge 409 that can help grip the slide 306. In some implementations, the textured edge 409 can be provided by a flexible material (e.g., rubber) that aids in gripping the slide 306.

The mounting plate 309 acts as a stage for microscopic examination of the sample slide 306. As shown in FIGS. 4A-4F, the mounting plate 309 includes an opening 412 that allows the light source 206 to illuminate the sample during image capture, when the slide 306 is positioned over the opening 412. The slide clamp 303 can utilize a spring assembly (e.g., a hold down spring) to apply downward pressure on the slide 306 to hold it against the mounting plate, which acts as a stage during microscopic imaging of the sample. A pressure plate 415 (FIGS. 4E and 4F) that extends over the alignment arm 403 and clamping arm 406 can be used to secure the hold down spring (or other spring assembly) in position on the slide clamp 303. A lower edge 418 (FIG, 4A) of the clamping arm 406 and/or the alignment arm 403 can be beveled outward to aid in holding the slide 306 against the surface of the mounting plate 309.

As previously discussed, the stepper or servo motor 330 (FIGS. 3A-38) can be used to control rotation of the slide clamp 303. The position of the slide clamp 303 can he detected using one or more sensors. In the example of FIGS. 4E and 4F, a sensor 421 is used to detect when the slide clamp 303 has been rotated to a reference position where the slide clamp 303 is aligned to receive a sample side 306 from or return the sample slide 306 to the carriage 106 (FIG. 1). A tab 424 affixed to the slide clamp 303 can be used to detect the position of the slide clamp 303 with the sensor 421 (e.g., a capacitive sensor, a magnetic sensor, an infrared sensor, a photosensitive sensor, etc.). For example, the tab 424 extends from a side of the slide clamp 303 such that it can he detected by the sensor 421 when the slide clamp 303 is oriented with the carriage 106, where can receive a sample slide 306. With the reference position known, the stepper or servo motor 330 can be controlled to position the sample slide 306 in the proper orientation for processing and for imaging.

For imaging, the sample slide 306 is positioned over the opening 412 of the mounting plate 309. To ensure that the alignment of the sample slide 306 over the opening 412 is repeatable, the mounting plate 309 can include a guide shoulder 427 opposite from the slide clamp 303 as illustrated in FIGS. 4A and 4B. The guide shoulder 427 can he machined or otherwise formed on the mounting plate 309 so that, as a sample slide 306 is rotated over the opening 412, the distal end of the slide 306 opposite the slide clamp 303 contacts the guide shoulder 427 to align the position along the longitudinal axis of the slide 306. The downward pressure applied by the spring assembly of the slide clamp 303 can hold the slide 306 against the mounting plate 309 and prevent the distal end of the slide 306 from moving over the guide shoulder 427. A slide stop 430 can be used to prevent the distal end of the slide 306 from moving beyond the desired orientation. The slide stop 430 can be machined or otherwise formed on the mounting plate 309 adjacent to the guide shoulder 427. The combination of the alignment arm 303, guide shoulder 427 and slide stop 430 allows for consistent positioning of sample slides 306 on the mounting plate 309 during imaging with the microscopic lenses 209 and image capture unit 212 (FIG. 3O). In addition, a sample slide 306 can be reinserted and positioned for reexamined at the same location at different times. The mounting plate 309 can include a backside groove (shoulder or boss) with a clamp stop 433 to provide a hard stop to ensure a 90 degree alignment and prevent over-rotation during positioning of the slide 306 under the digital microscope. Consistency of positioning allows the slide processing unit 100 to relocate image positions on the sample slide 306 after it has been removed and replaced.

Referring back to FIGS. 3A-3D, the movement of a slide 306 by the slide positioner 203 is illustrated. As shown in FIG. 3A, the slide positioner 203 includes a slide clamp 303 that grips a sample slide 306 when inserted through the carriage 106. With the carriage 106 closed, a proximal end of the sample slide 306 extends into the slide processing unit 100. With the slide clamp 303 rotated to the reference position as detected by sensor 421 (FIGS. 4E-4F), the stepper or servo motors 321 can be controlled to align the slide clamp 303 with, but offset from, the proximal end of the sample side 306. In some embodiments, this can be a default position when no slide 306 is being handled by the slide processing unit 100. The slide positioner 203 can then be advanced along the y-axis by stepper or servo motor 321*b* to secure the proximal end of the sample slide 306 between the alignment arm 403 and clamping arm 406 of the slide clamp 303. Pressure from the clamping arm 406 forces the opposite side of the slide 306 against the alignment arm 403, which properly orients the slide 306 in the slide clamp 303.

The slide clamp 303 can also include a spring assembly for holding the slide 306 in position on the mounting plate. For example, a hold down spring can be configured to apply downward pressure on the top of the slide 306 to avoid twisting of the slide 306 in the slide clamp 303. In other embodiments, the inner surface of the alignment and clamping arms 403 and 406 can be tapered or beveled outward from top to bottom such that a force is applied to the top edges of the sides of the slide 306 to avoid twisting in the slide clamp 303. With the slide clamp 303 holding the proximal end of the sample slide 306, the slide positioner 203 can then be retracted along the y-axis by stepper or servo motor 321*b* to remove the slide 306 from the carriage 106. With the sample slide 306 clear of the carriage 106, the slide positioner 203 can reposition the slide 306 along the x-axis and y-axis by moving along the rails 312 and 318, as well as by rotating the slide 306 about the z-axis.

For example, a small drop of blood can be placed on an enumerated location on an unprepared glass microscope slide 306. The sample slide 306 can then be placed in the carriage 106 (FIGS. 1-2) and inserted into the slide processing unit 100. The slide clamp 303 may then be positioned to grip the proximal end of the slide 306 as illustrated in FIG. 3A. The carriage 106 is not shown for illustration. Pressure from the clamping arm 406 forces the slide 306 against the alignment arm 403 as depicted. The slide positioner 203 can than draw the slide 306 out of the carriage 106 and reposition it for processing of the sample. For example, the slide clamp 303 can rotate about 90 degrees for smearing and/or treatment of the blood sample as shown in FIG. 3B.

In one embodiment, the sample slide 306 is positioned so that a second smearing slide (not shown) drops down to contact the slide at a predefined angle (e.g., about 45 degrees). With the smearing slide resting on the sample slide 306, the slide processing unit 100 can advance the mounting plate 309 along the first pair of slide rails 312 such that the sample slide 306 moves forward until a short edge of the smearing slide reaches the enumerated location, where it contacts and waits momentarily for capillary action to fully engage the blood droplet along the edge of the smearing slide. In some implementations, the slide processing unit 100 can be configured to optically detect when the sample has reached the smearing slide using one or more sensors and/or light sources. The slide 306 is then backed out from under the smearing slide, allowing capillary action to smear the blood along the length of the slide 306. In this way, a monolayer of cells can be achieved along at least a portion of the resulting sample smear. The slide 306 with the sample continues to be retracted until the smearing slide drops off the end of the sample slide 306 and falls to the bottom of the slide processing unit 100 where it becomes waste. In some implementations, a drawer in the bottom of the slide processing unit 100 can catch the falling slides so that they can be retrieved by a user for disposal or cleaning and reuse. The mounting plate 309 can again position the slide 306 for further processing of the sample.

The slide 306 with the smeared sample can be moved to a desiccation position where it is air or vacuum desiccated for a brief period of time by a small fan in the slide processing unit 100. Once the smeared sample is desiccated, the slide 306 travels forward as shown in FIG. 3B to be positioned under a slide treatment system containing, e.g., methanol which is sprayed, using micro streams of fluid, over the entire surface of the slide 306. The position of the slide 306 can be incrementally controlled along the x-axis and y-axis by the stepper or servo motors 321. This process "fixes" the slide 306. The slide 306 can then be returned to the desiccation position and the methanol evaporated using forced air. In some embodiments, a vacuum can be used to desiccate the treated sample by drawing air across the slide 306 towards a suction tube located adjacent to the slide 306.

The slide 306 can then be moved forward to one or more treatment positions that each can, in sequence, spray a liquid stain (or other chemical treatment) onto all or a portion of the sample. Various stains or other treatments can be discharged through electronically controlled jet nozzles. Additional rinsing with alcohol and/or other solvents can be accomplished as previously described to provide for Gram staining of slides. A reservoir in the bottom of the slide processing unit 100 can collect any overflow liquid from the slide 306. A drain connection can allow the overflow liquid to drain from the reservoir into an appropriate disposal system.

When the slide preparation is completed, the slide 306 can be moved under a digital microscope as shown in FIG. 3G. The digital microscope includes lenses 209 and image capture unit 212, which includes mirrors, lenses, and/or an imaging device 803 such as, e.g., CCD's or CMOS circuitry. An image of the sample on the slide 306 can be digitized automatically in a mosaic fashion and stored in memory. The digitized image can be made visible to either the local operator on the display screen 103 (e.g., a self-contained high resolution color monitor) and/or sent via the Internet and/or intranet for review by others skilled in the art of pathology. Focus may be adjusted by adjusting the position of the microscopic lenses 209 over the slide 306. The light source 206 illuminates the sample during image capture. FIG. 3D illustrates the position of the slide 306 over the light source 206 with the image capture unit 212 removed from view.

Figure 5A:
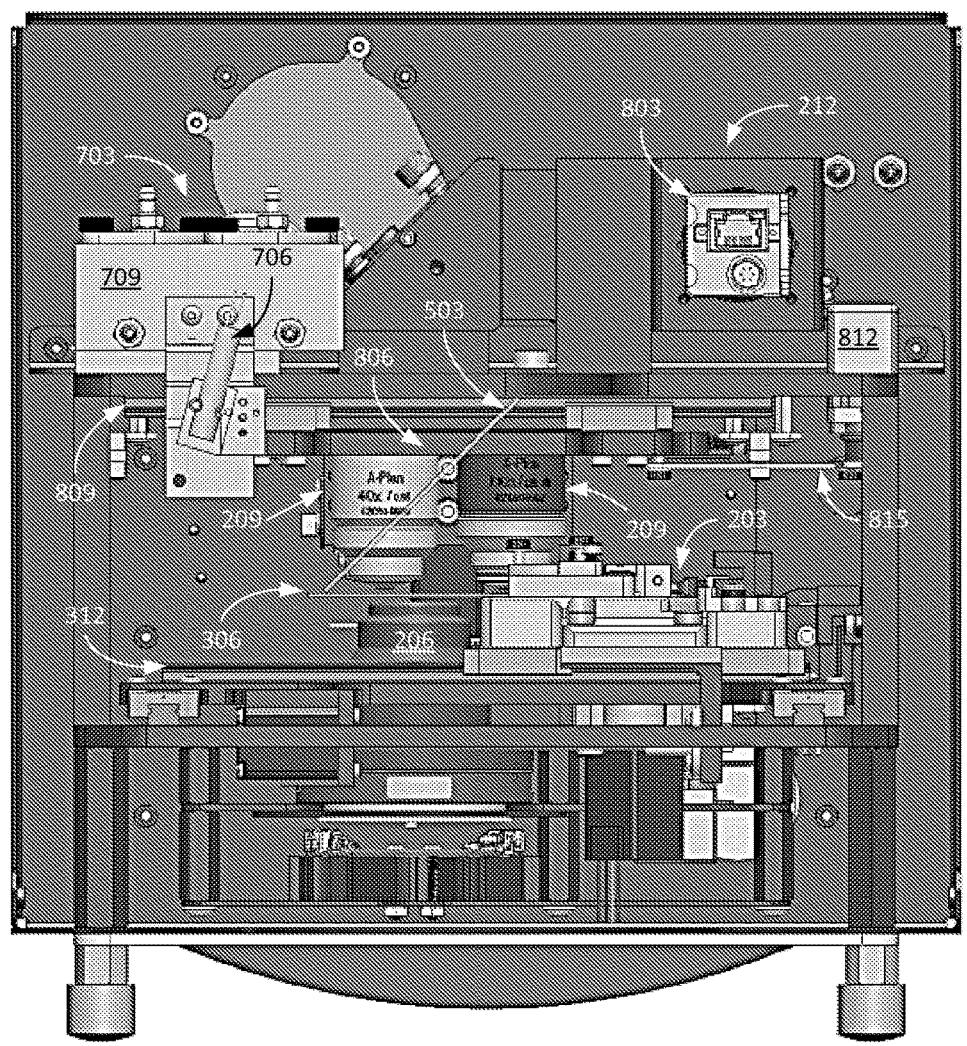
FIGS. 5A and 5B-5D are front and perspective views (respectively) of an example of the interior of the slide processing unit of FIGS. 1 and 2 in accordance with various embodiments of the present disclosure.
Figure 5B:
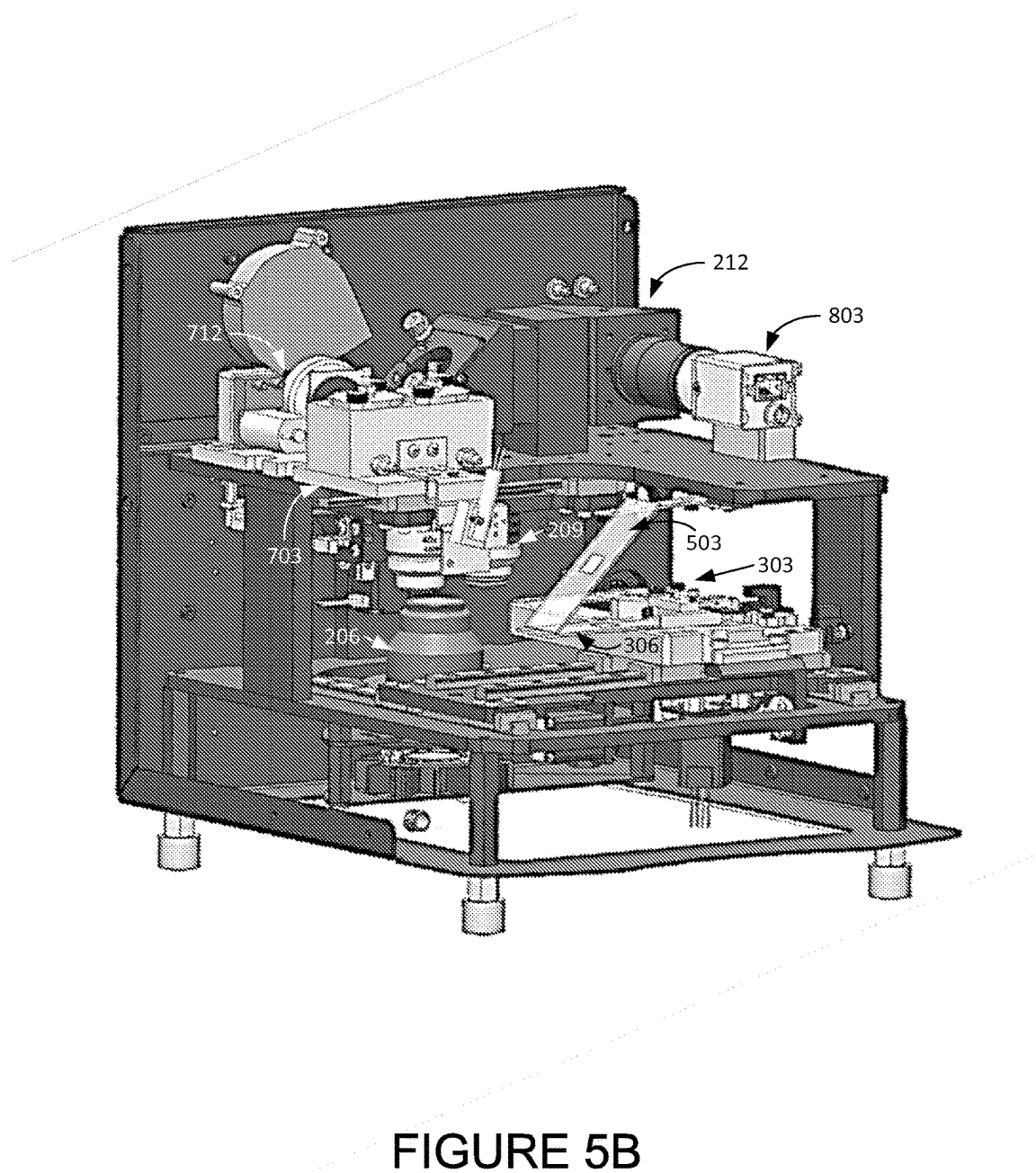

Referring to FIGS. 5A through 5D, shown are various views of an interior of the slide processing unit 100 that illustrate the orientation of the smearing slide 503 with respect to the sample slide 306. As can be seen in FIG. 5A, the sample slide 306 is positioned so that the smearing slide 503 makes contact at a predefined angle (e.g., about 45 degrees). By allowing the smearing slide 503 to freely move or rock when making contact with the sample slide, the short edge of the smearing slide 503 can rest evenly across the width of the sample slide 306. With the smearing slide 503 resting on the sample slide 306, the slide processing unit 100 can advance the mounting plate 309 along the first pair of slide rails 312 such that the sample slide 306 moves forward until a short edge of the smearing slide contacts the blood droplet and allows capillary action to draw it across the edge of the smearing slide 503. After waiting for a predefined period to avow for the capillary action, the slide processing unit 100 can retract the mounting plate 309 along the first pair of slide rails 312 such that the sample slide 306 moves backward, which smears the blood sample along the length of the sample slide 306. As the sample slide 306 is retracted from under the smearing slide 503, the smearing slide 503 can drop to the bottom of the slide processing unit 100 where it can be retrieved from at a later time. For example, a drawer or other access can be included to allow the discarded slides to be retrieved by a user for cleaning and reuse or for appropriate disposal.

In other implementations, the smearing slide 503 can be advanced on the sample slide 306 until the short edge reaches the enumerated location and then withdrawn to smear the blood along the length of the slide 306. In some embodiments, a filament (e.g., a multi-fiber or mono filament) may be used instead of the smearing slide. The filament can extend across the width of, and resting on top of, the slide 306 between two spools (e.g., a dispensing spool and a take-up spool). The slide 306 can be advanced and withdrawn to smear the blood along the length of the slide 306. After the filament is clear of the slide 306, the soiled portion of the filament may be wound up on the take-up spool while a clean portion of the filament is uncoiled from the dispensing spool.

FIGS. 6A through 6D illustrate an example of a slide dispenser unit 603 that can be used to dispense smearing slides 503 onto the sample slide 306. In this embodiment, the slide dispenser unit 603 includes a smearing slide magazine 606 configured to hold one or more smearing slides 503 and discharge single smearing slides 503 into a slide sled 609 from an end of the smearing slide magazine 606. After a sample slide 306 with a sample is received by the slide clamp 303, the slide positioner 203 can reposition it for smearing of the sample. A smearing slide 503 can be dispensed from the smearing slide magazine 606 by moving down a slide sled 609 and contacting the sample slide 306 at an angle in the range of about 30 degrees to about 60 degrees (e.g., 45 degrees). The smearing slide 503 can be dispensed from the smearing slide magazine 606 using, e.g., a blade that extends to push the smearing slide 503 out of the smearing slide magazine 606 or a wheel that turns to push the smearing slide 503 out of the smearing slide magazine 606.

As the smearing slide 503 leaves the smearing slide magazine 606, it drops into the slide sled 609 where it slides down until contacting the sample slide 306 located below. A holding bar 612 extending across the distal end of the slide sled 609 holds the smearing slide 503 in the slide sled 609 when the sample slide 306 is moved forward during smearing. The holding bar 612 can include a pivot point that extends toward the bottom of the trough of the slide sled 609 to allow the smearing slide 503 to rock about the center point (side-to-side) when making contact with the sample slide 306. For example, the holding bar 612 can have a shallow v-shape with the center point providing the pivot point or can include a point or tip that extends downward from the center of the holding bar 612 to provide the pivot point. The pivot point allows the and of smearing slide 503 to self-align with the surface of the sample slide 306, which aids in the capillary action during smearing. The weight of the smearing slide 503 provides the contact pressure onto the slide 306 with the sample.

Figure 6A:
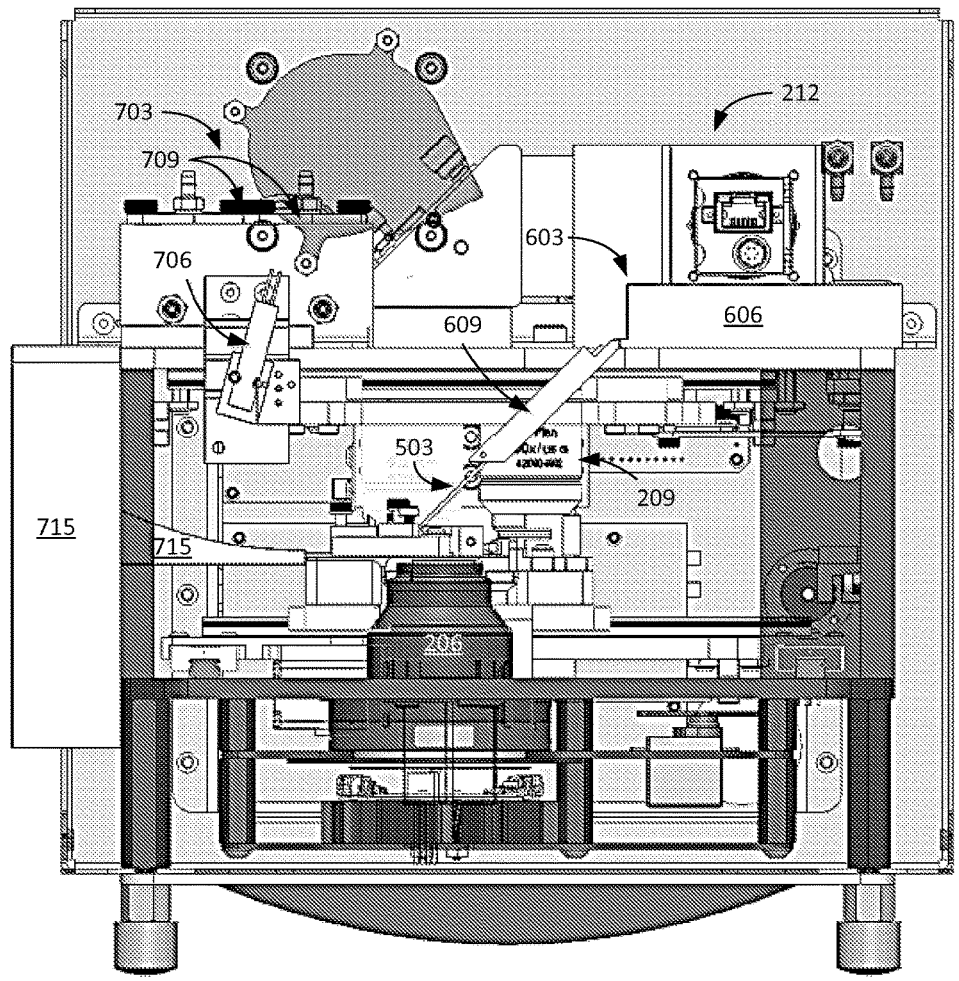
FIGS. 6A and 6B-6C are front and perspective views (respectively) of an example of the interior of the slide processing unit of FIGS. 1 and 2 including a slide dispenser unit in accordance with various embodiments of the present disclosure.
Figure 6B:
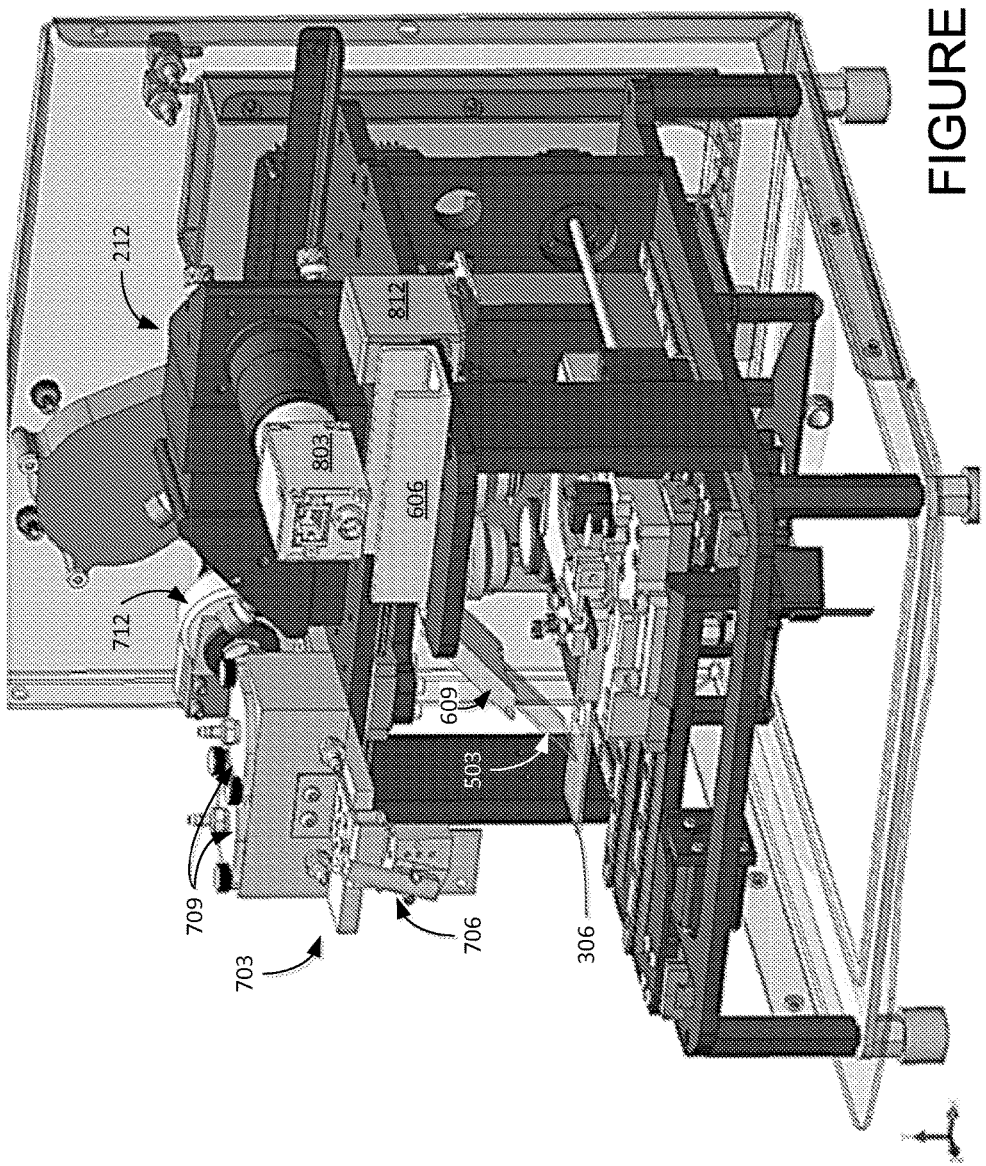
Figure 6C:
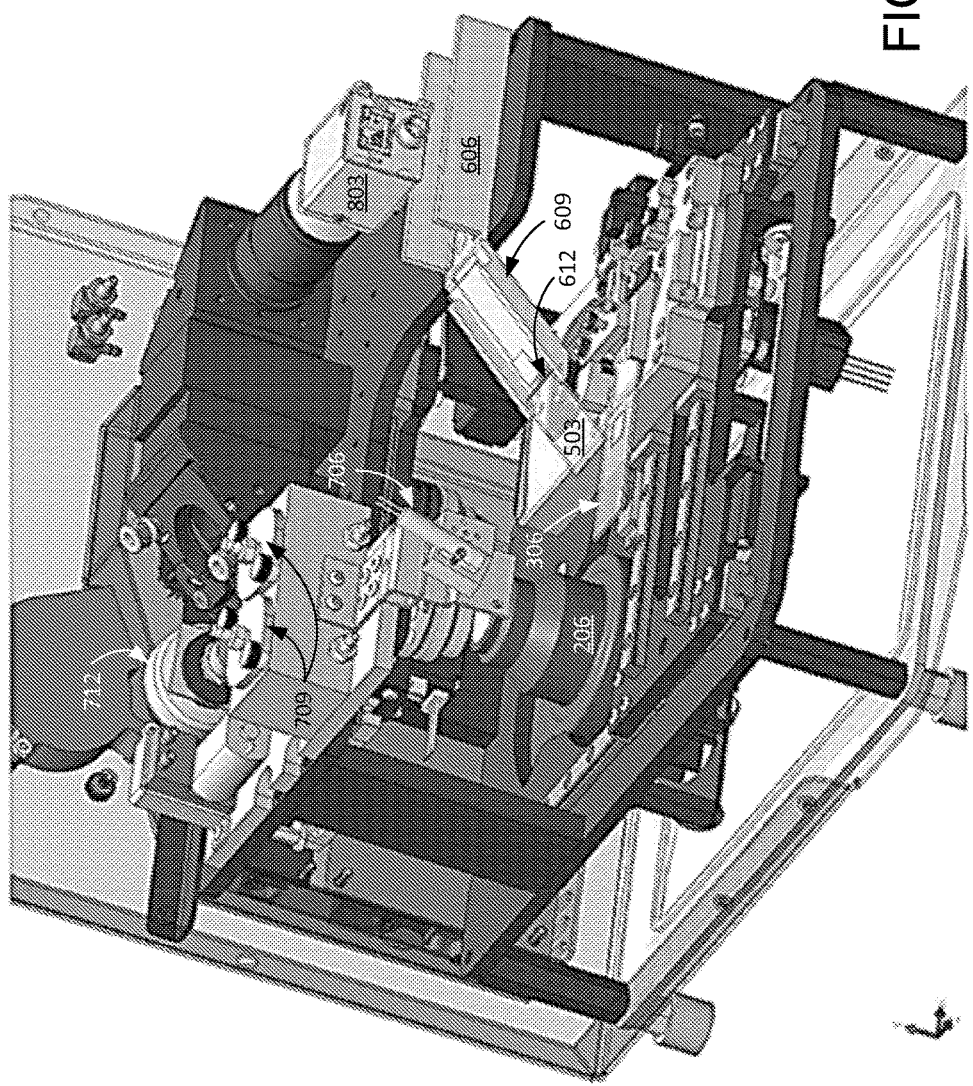

A hinged joint between the slide magazine 606 and slide sled 609, which can be controlled using a servo or stepper motor, allows the contact angle to be adjusted. In the example of FIGS. 6A-6C, the smearing slide 503 contacts the slide 306 with the sample at an angle of about 45 degrees. A capped pin (e.g., a stud, screw, bolt, etc.) can be located at the proximal end of the slide sled 609 such that it extends upward from the bottom of the trough. When the smearing slide 503 is dispensed, it moves over and past the top of the capped pin as it travels down the trough of the slide sled 609. When the smearing slide 503 reaches the sample slide 306, the capped pin can press against the opposite end of the smearing slide 503 to restrict movement of the smearing slide 503 back up the slide sled 609 when the sample slide 306 is retracted during smearing. The cap at the top of the capped pin catches the lip of the smearing slide 503 to prevent it from moving back over the top of the capped pin.

With the smearing slide 503 in position on the sample slide 306, the slide positioner 203 can advance the slide 306 until the sample contacts the lower edge of the smearing slide 503 and wait momentarily for the capillary action to fully engage the sample with the lower edge and form a meniscus. The sample slide 306 can then be retracted allowing the capillary action to smear the blood along the length of a e slide 306. The slide 306 with the sample continues to retract until the smearing slide 503 drops off the end of the slide 306 and into the bottom of the slide processing unit 100. The used smearing slide 503 can be cleaned and sterilized for reuse or can be disposed of appropriately. The slide 306 with the smeared sample can then be moved to a desiccation position where the smeared sample is air desiccated for a brief period of time by a small fan in the slide processing unit 100.

Figure 7E:
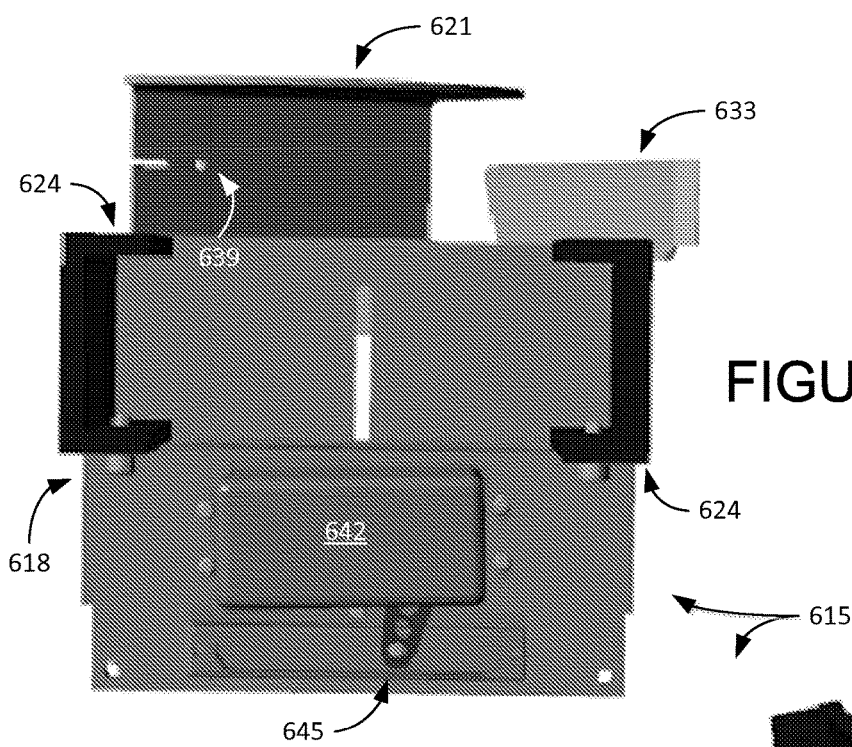
Figure 7F:
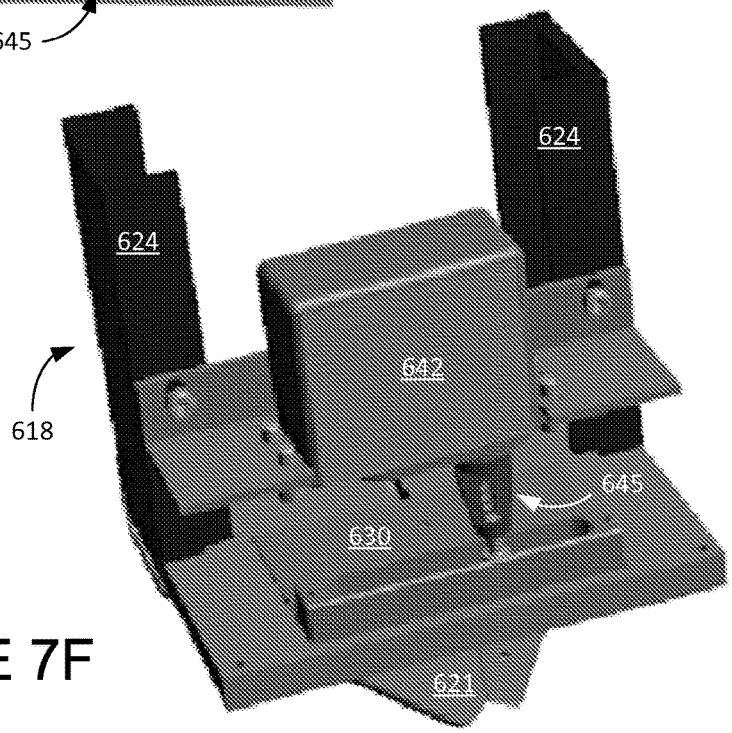
Figure 7G:
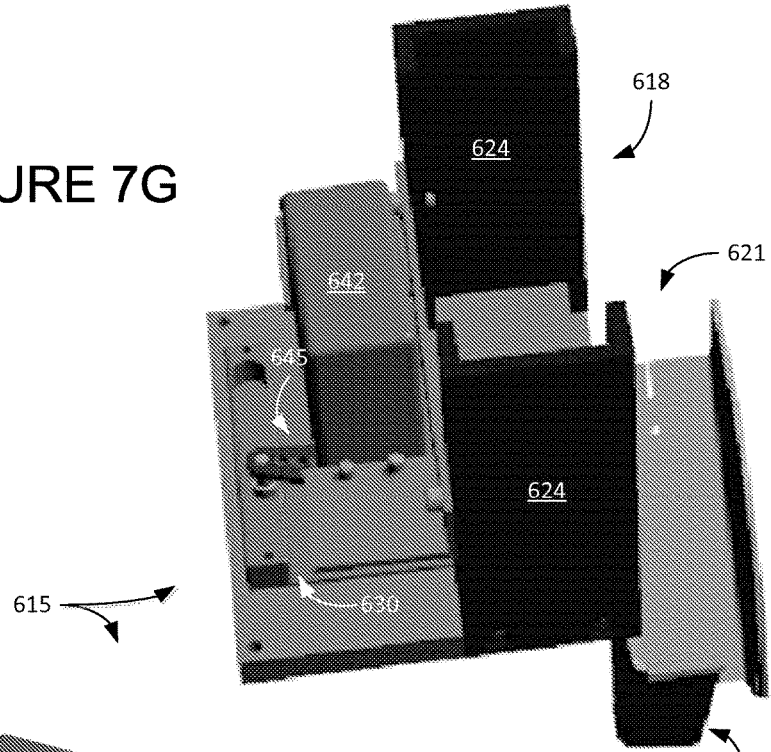
Figure 7H:
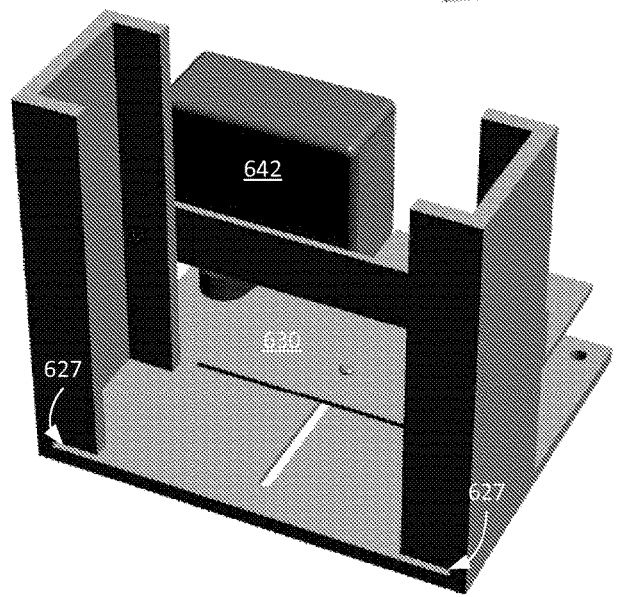

Referring to FIGS. 7A through 7H, shown are various views of another example of a slide dispenser unit 615 that can be utilized in the slide processing unit 100. FIGS. 7A and 7D provide front and back views (respectively). FIGS. 7B and 7C provide left and right side views (respectively). FIG. 7E provides a top view, and FIGS. 7F-7H provide various perspective views of the slide dispenser unit. In this embodiment, the slide dispenser unit 615 includes a smearing slide magazine 618 configured to hold one or more smearing slides 503 and discharge single smearing slides 503 into a slide sled 621 from a side of the smearing slide magazine 618. The smearing slides 503 are held in position by stacking guides 624 that include a gap 627 at the bottom to allow a single smearing slide 503 to be dispensed from the bottom of a stack.

After a sample slide 306 with a sample is received by the slide clamp 303, the slide positioner 203 can reposition it for smearing of the sample. A smearing slide 503 can be dispensed from the smearing slide magazine 618 by a blade 630 that extends to push the smearing slide 503 out of the smearing slide magazine 618 and into the slide sled 621 and then retracts back to allow the next slide in the stack to move into position for dispensing. In the example of FIGS. 7A-7H, the smearing slide 503 drops into the trough of the slide sled 621 and it guided to the bottom by an end wall 633 and side walls of the slide sled 621. The bottom of the slide sled 621 is set at a predefined angle (e.g., about 45 degrees) that controls the angle of contact with the sample slide 306. When the smearing slide 503 reaches the bottom of the trough, the smearing slide 503 moves forward under the bottom of the end wall 633 (as illustrated in FIGS. 7A and 7D) until it reaches the sample slide 306. With the smearing slide 503 resting on the bottom of the slide sled 621, the weight of the smearing slide 503 provides the contact pressure onto the sample slide 306. The slide sled 621 can be placed approximately the same location as the slide sled 609 shown in FIGS. 6A-6C.

The end wall 633 of the slide sled 621 holds the smearing slide 503 in the slide sled 621 when the sample slide 306 is moved forward during smearing. As seen in FIG. 7B, the end wall 633 includes a pivot point 6 6 that extends toward the centerline of smearing slide 503 to allow the smearing slide 503 to rock about the center point (side-to-side) when making contact with the sample slide 306. The pivot point 636 allows the end of smearing slide 503 to self-align with the surface of the sample slide 306, which aids in the capillary action during smearing. A capped pin (e.g., a stud, screw, bolt, etc.) can be located at the upper end of the slide sled 621 such that it extends upward from the bottom of the trough. For example, a small screw or bolt can be secured through a hole or opening 639 in the slide sled 621. When the smearing slide 503 is dispensed, it moves over and past the top of the capped pin as it travels down the trough of the slide sled 621. When the smearing slide 503 reaches the sample slide 306, the capped pin can press against the opposite end of the smearing slide 503 to restrict movement of the smearing slide 503 back up the slide sled 621 when the sample slide 306 is retracted d ring smearing. The cap at the top of the capped pin catches the lip of the slide 706 to prevent it from moving back over the top of the capped pin.

When the smearing slide 503 is ejected, the blade presses against an edge of the bottom slide of a stack of slides in a slide magazine. An electric motor 642 (or solenoid) rotates a lever arm 645 to push the blade forward against a side of the bottom slide. For example, a rod at the end of the lever arm 645 can move inside, a channel or groove to translate the rotational motion of the lever arm 645 into linear motion of the blade 630. Linear motion of a blade 630 can be ensured using guide pins in a groove. The thickness of the blade 630 is less than the thickness of a smearing slide 503 and the height of the gap 627 is more than the thickness of a smearing slide 503, but less than twice the thickness of the slides, to avoid dispensing more than one slide at a time.

The pivot point 636 of the slide sled 621 holds the smearing slide 503 in position while the sample slide 306 is moved forward by the slide clamp 303 until the edge of the smearing slide 503 contacts the sample. At that point, capillary action draws the sample across the edge of the smearing slide 503. The sample slide 306 can then be retracted while the smearing slide 503 pulls the sample along the surface of the sample slide 306. The capped pin of the slide sled 621 holds the smearing slide 503 in position while the sample slide 306 is moved back by the slide clamp 303. As the end of the smearing slide 503 passes over the end of the sample slide 306, the smearing slide 503 drops out of the slide sled 621 into the bottom of the slide processing unit 100 (e.g., the reservoir or a collection drawer). The slide 306 with the smeared sample can then be moved to a desiccation position where the smeared sample is air or vacuum desiccated for a brief period of time. In some embodiments, a vacuum can be used to desiccate the treated sample by drawing air across the sample slide 306 towards a suction tube located adjacent to the slide 306. In other implementations, forced air can be blown on the sample slide 306 by a small fan in the slide processing unit 100.

Once desiccated, the sample slide 306 can be positioned under the slide treatment system 703 for staining and/or other chemical treatment of the sample. Referring next to FIGS. 8A through 8F, shown are various views of an example of the slide processing unit 100 including the slide treatment system 703 for staining and/or other chemical treatment of the sample on the slide 306. The slide treatment system 703 includes one or more jet nozzles 706 for application of a fluid (e.g., stain, water, air, oil or other chemical) to the sample on the slide 306. The slide treatment system 703 also includes one or more reservoirs 609 for holding the treatment fluids. The fluids can be provided through external supply lines attached to corresponding jet nozzles 706 or from a reservoir 709 that is attached to a jet nozzle 606 through an internal supply line and pressurized using pressure regulated air or other appropriate gas. The slide processing unit 100 can include one or more pressure regulators 712 to ensure that appropriate pressure is applied to the reservoirs 709 for control of the jet sprays. The jet nozzles 706 can be electronically controlled to emit pulsed bursts of fluid for a predefined period of time (e.g., 20 µsec).

Figure 8A:
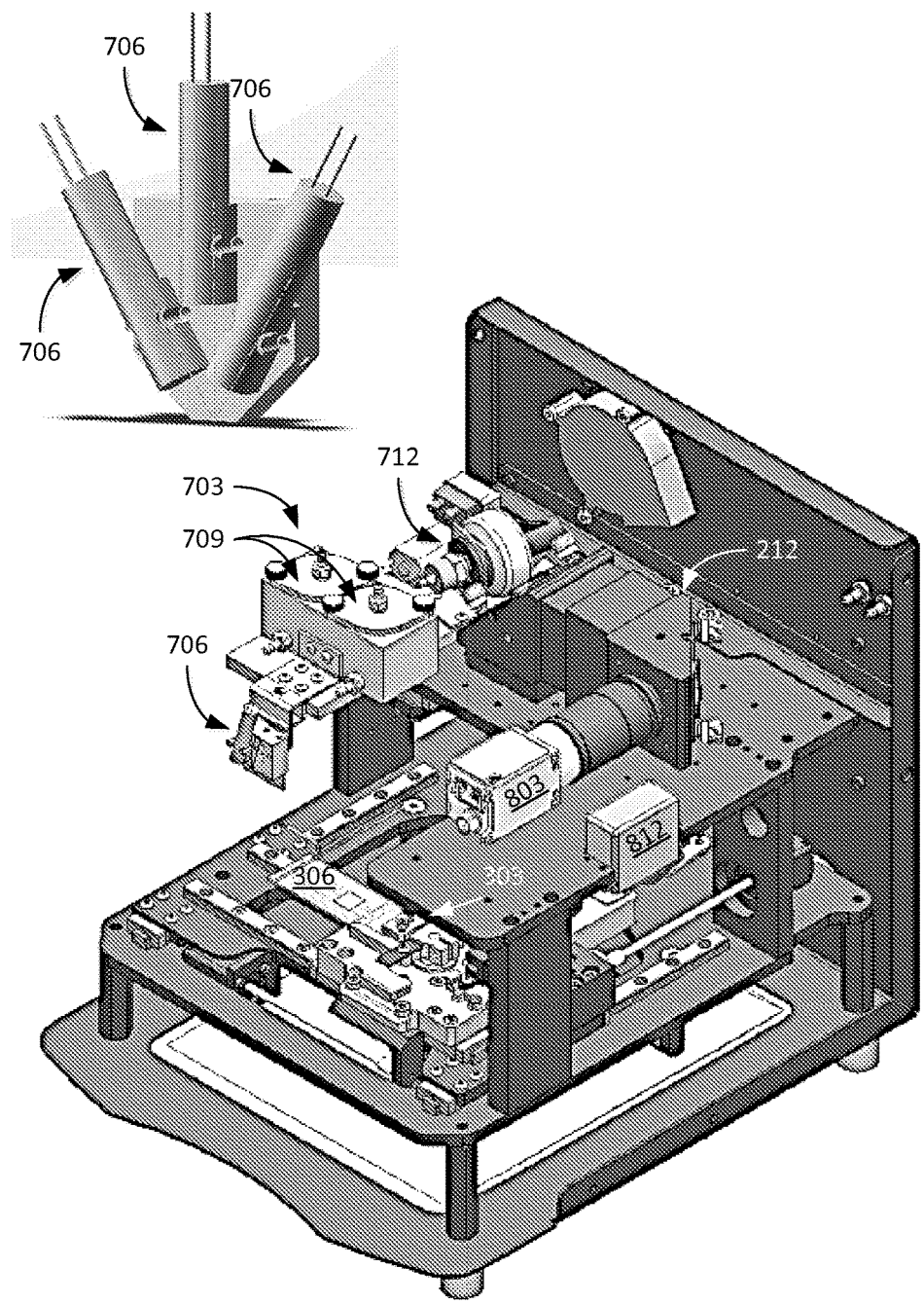

The jet nozzles 706 can be aligned to focus the fluid spray or micro streams at a known or common location on the surface of the slide 306. By positioning the jet nozzles 706 at a fixed position above the sample slide 306 and controlling the pressure of the applied fluid, a well-defined application area can be provided. FIG. 8A shows an example of a multi-nozzle arrangement including three jet nozzles 706 that are configured to apply treatment fluids. The jet nozzles 706 can be aligned so that different fluids can be applied to the same location on the sample slide 306 without movement of the slide 306. For example, four jet nozzles 706 can be arranged and aligned to direct different fluid sprays (e.g., a fixative, a stain, a water wash, and/or an air blast for drying) at a predetermined location. One or more stains and/or fixatives can be stored in individual reservoirs 709, while the water and air may be supplied from an external source. In other embodiments, some or all of the jet nozzles 706 may be aligned to different locations on the surface of the slide 306.

Figure 8B:
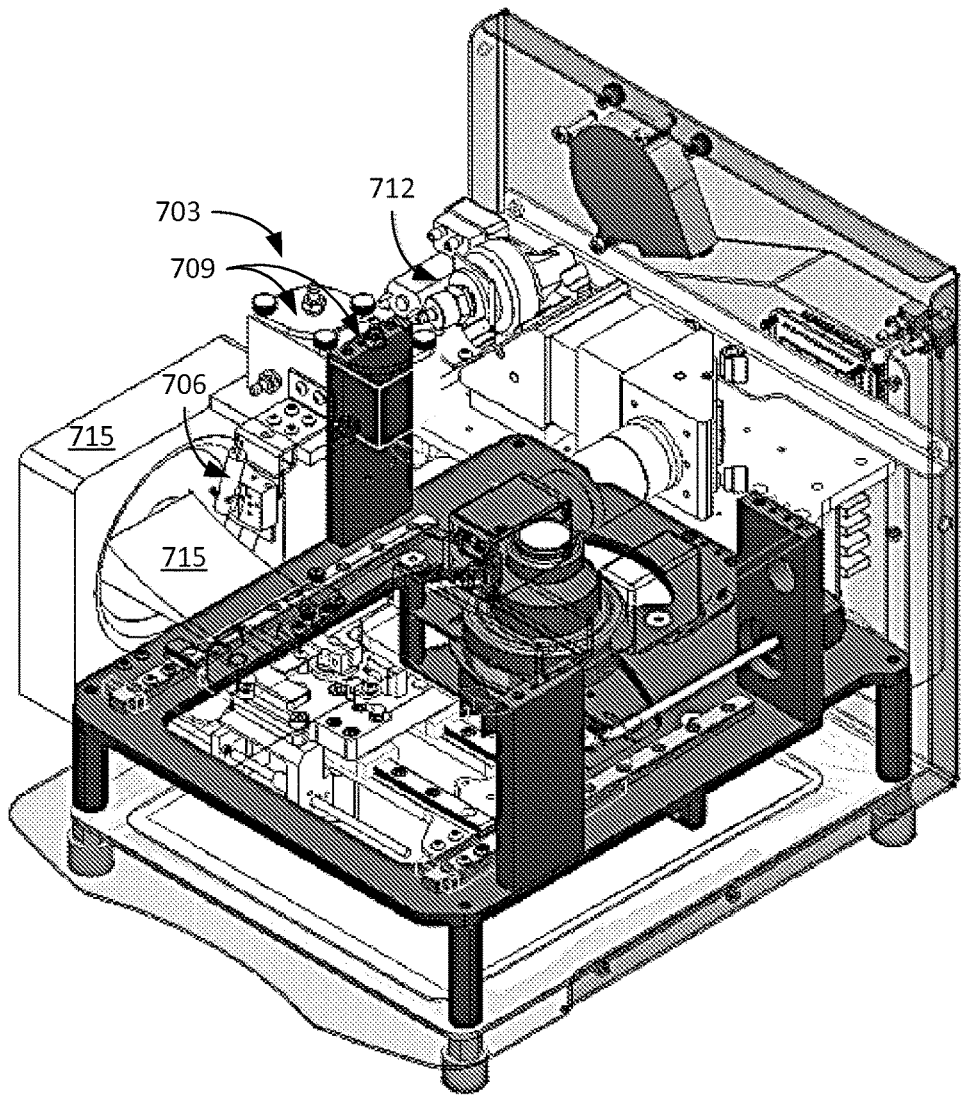
Figure 8D:
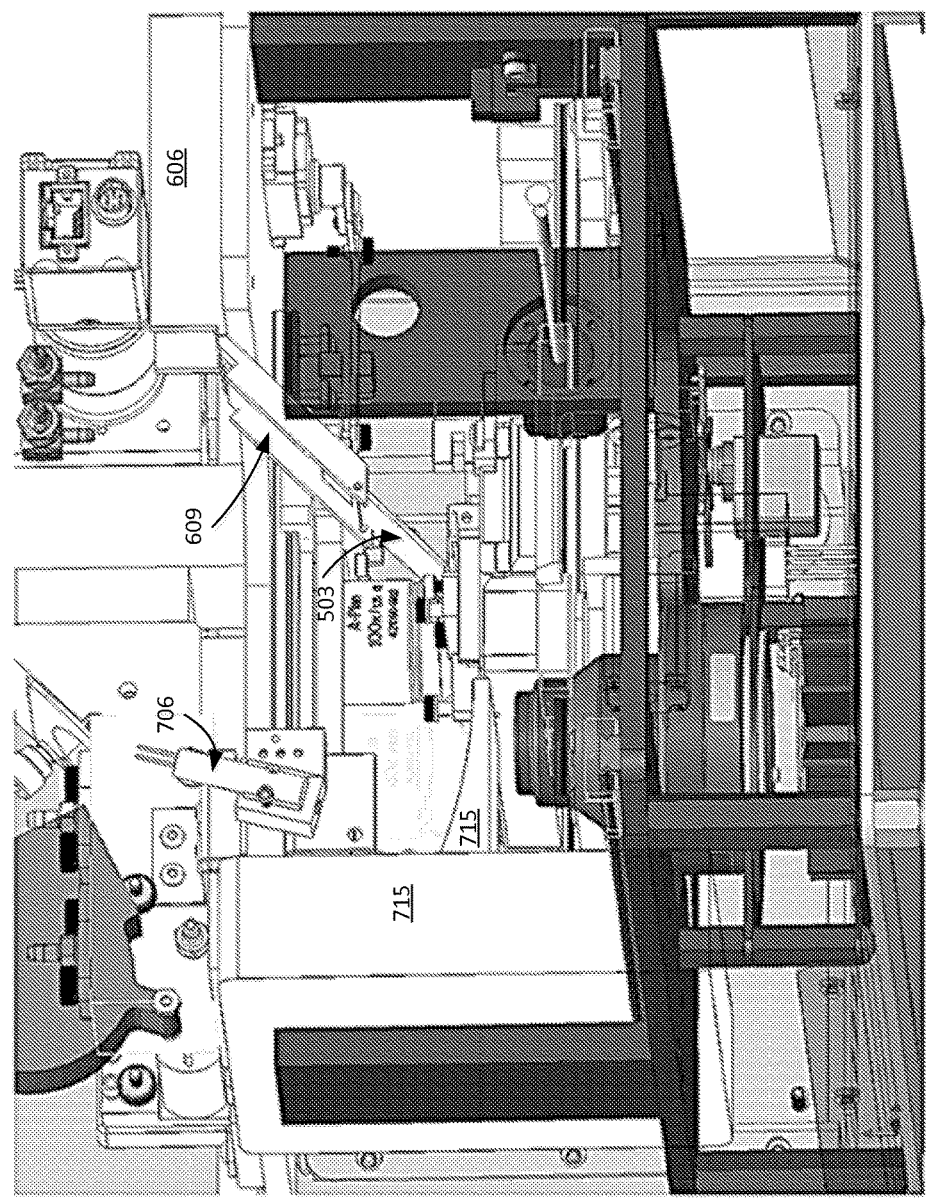
Figure 8E:
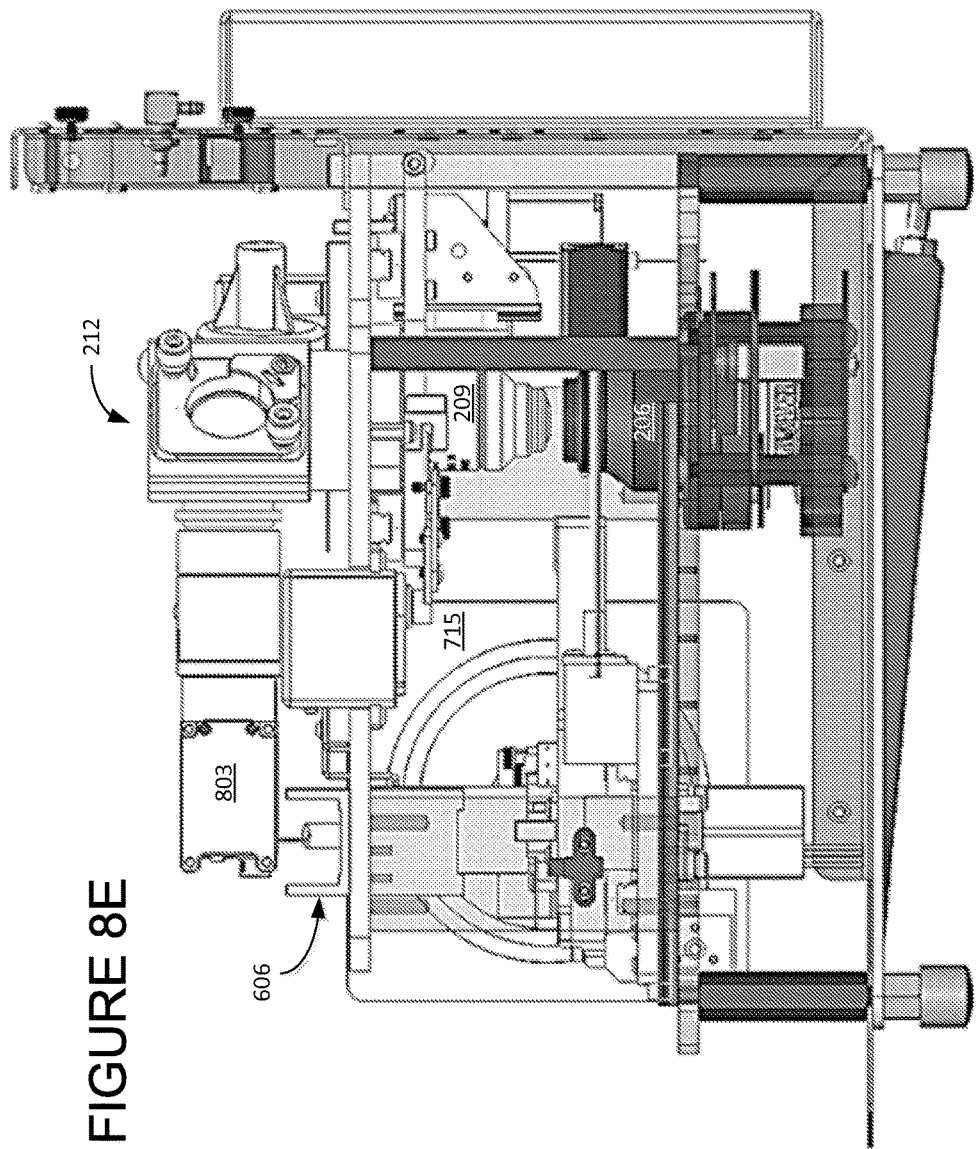

The fluids may be applied to the sample on the slide using short pulses while the position of the slide 306 is varied by the slide positioner 203 (or slide manipulation mechanism). In this way, various stains or other chemical treatments can be applied to different portions of the smeared sample on the slide 306. For instance, a stain may be applied to a defined area of the smeared sample after application of a fixative. A water wash may then be applied to remove excess material and a series of air blasts or vacuum applied to dry the sample. Excess fluids can flow off the slide 306 and into a reservoir in the bottom of the slide processing unit 100 for disposal or draining. As shown in FIGS. 8B and 8F, a backsplash 715 can be provided to minimize dispersion of the fluids during treatment of the slide 306. The slide positioner 203 can position the slide 306 under the jet nozzles 706 and over the backsplash 715 for application of the fluids to the smeared sample. In some implementations, oil may be deposited on the treated sample in order to enhance focusing and imaging.

Referring now to FIGS. 9A through 9D, shown in an example of another slide treatment system in accordance with various embodiments of the present disclosure. FIG.

Figure 9A:
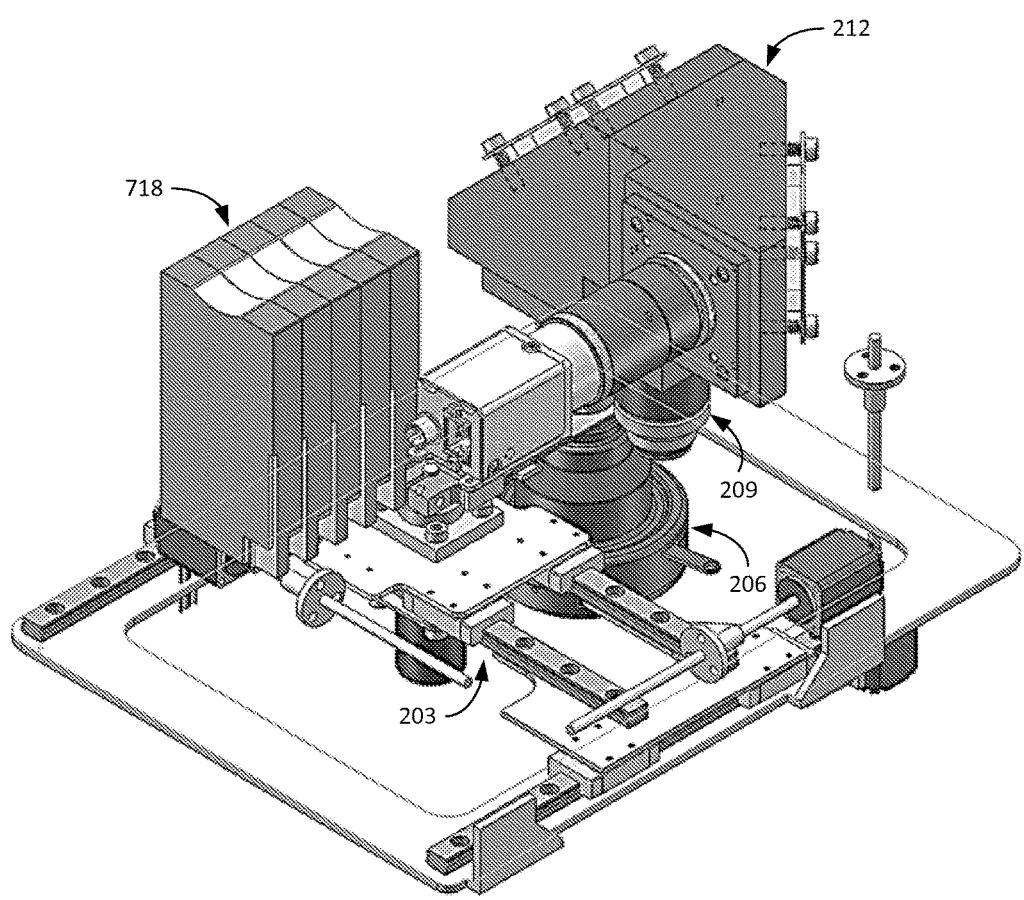
FIGS. 9A-9D are perspective, side, front and top internal views (respectively) of another slide treatment system of the slide processing unit of FIGS. 1 and 2 in accordance with various embodiments of the present disclosure.
Figure 9B:
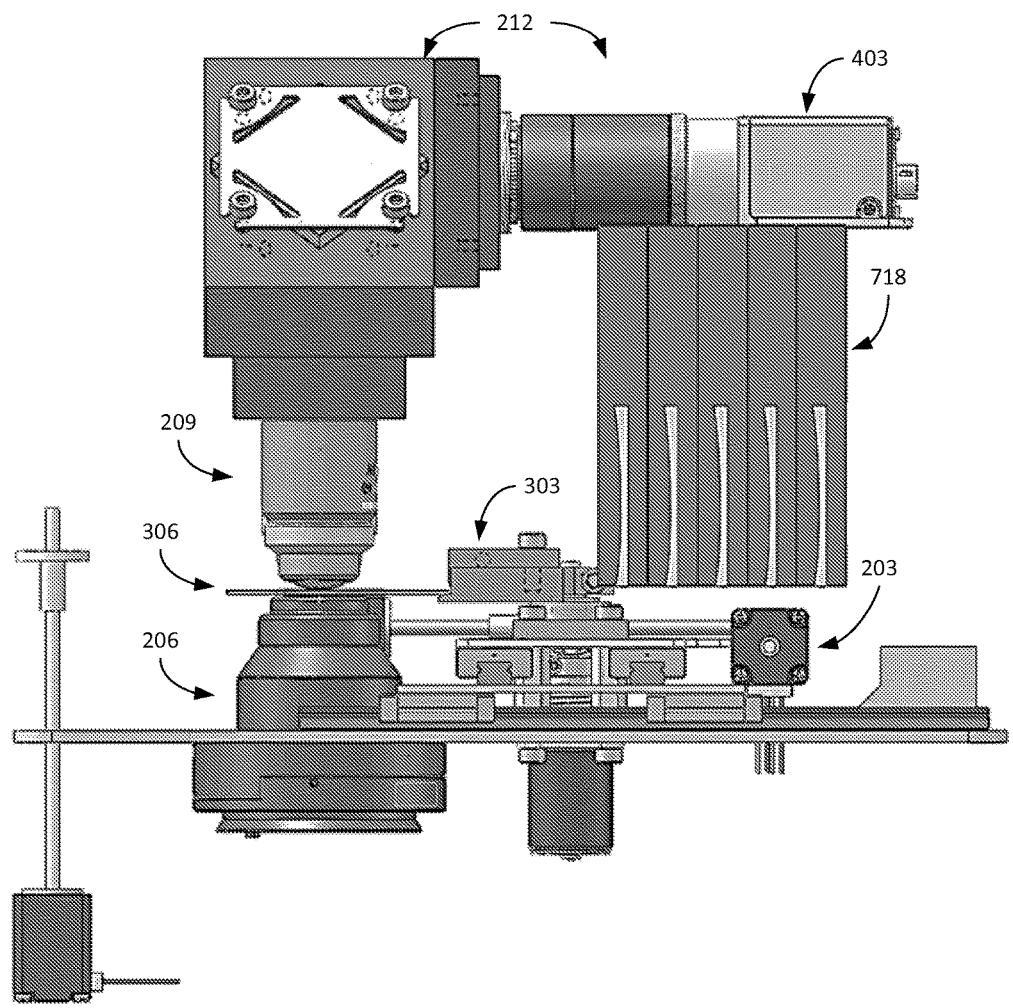
Figure 9C:
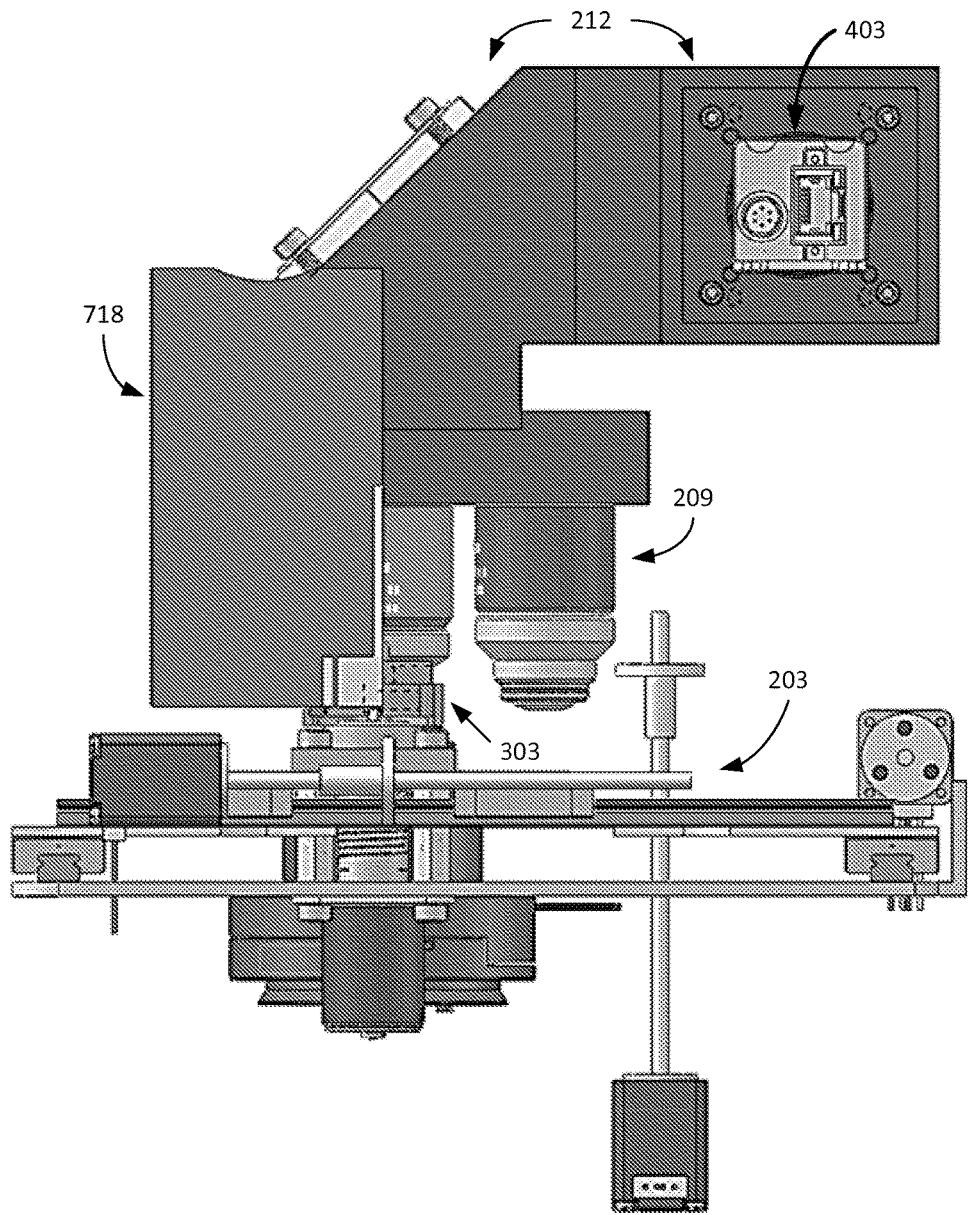
Figure 9D:
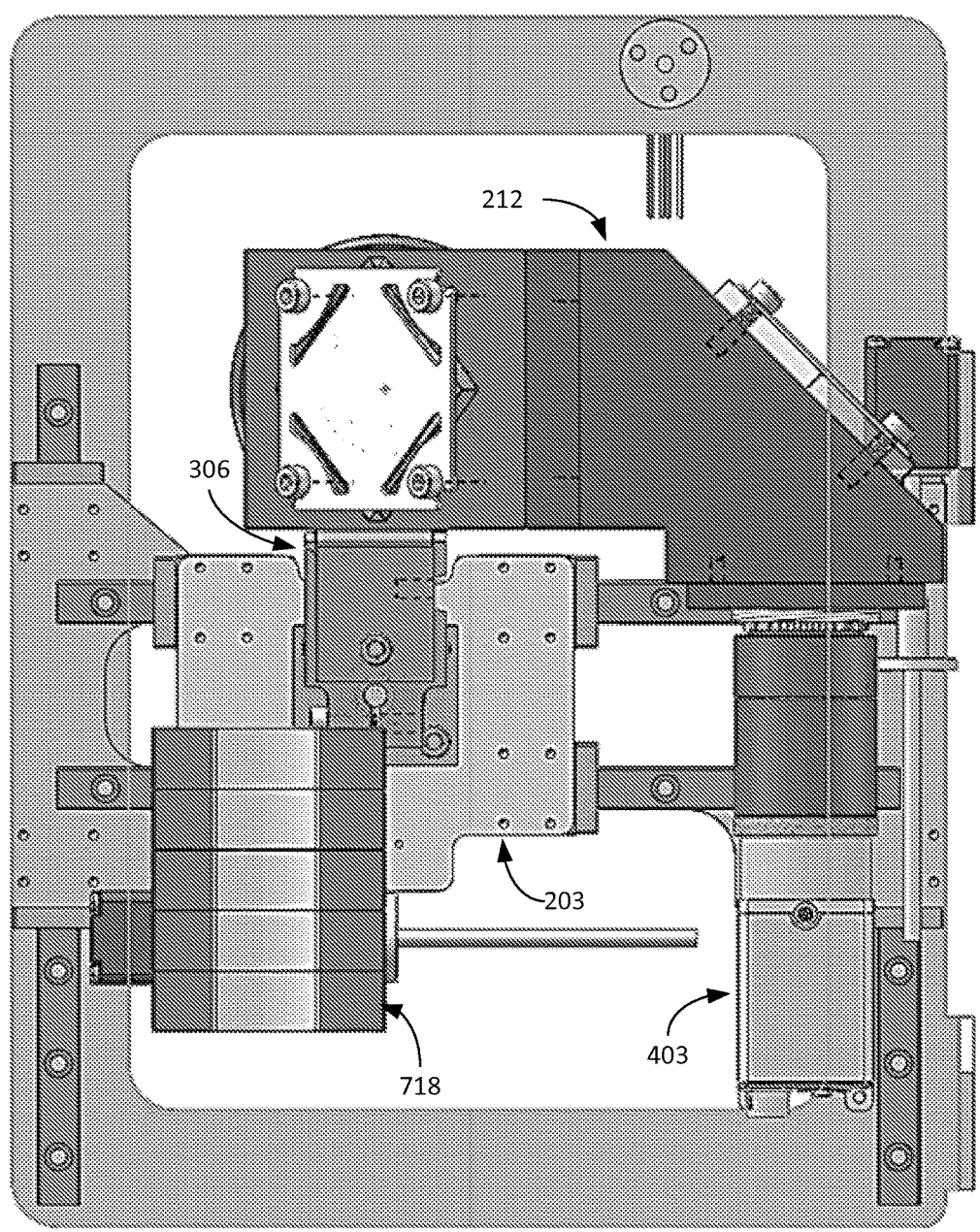

9A shows a perspective view and FIGS. 9B-9D show side, front and top internal views (respectively) of the slide processing unit 100. The slide processing unit 100 includes a slide treatment system having one or more cartridges 718. The cartridges 718 can hold stains or other chemicals for treatment of the sample on the slide 300 The stain or other chemical can be applied using deflected micro streams in a manner similar to ink jet printers. By adjusting the position of the sample slide 306 under the nozzles of the cartridges 718, treatment of the smeared sample can be controlled.

Figure 5C:
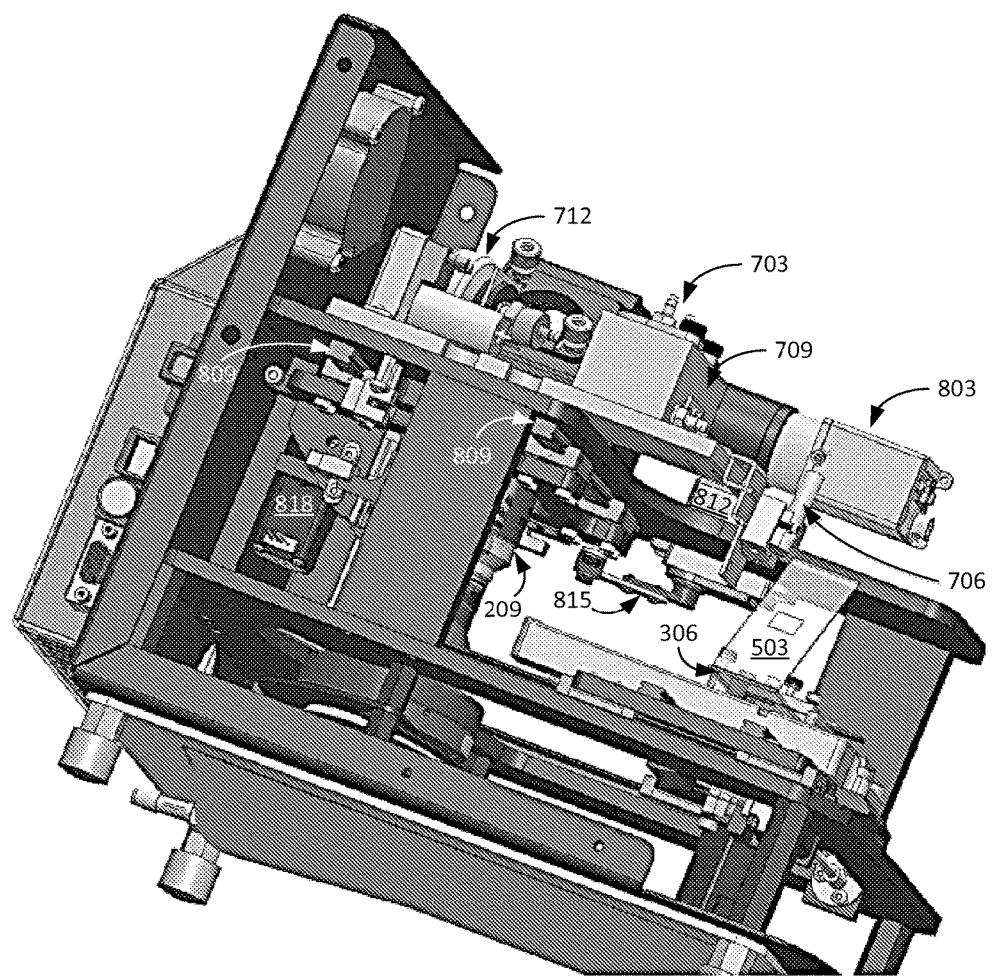
Figure 5D:
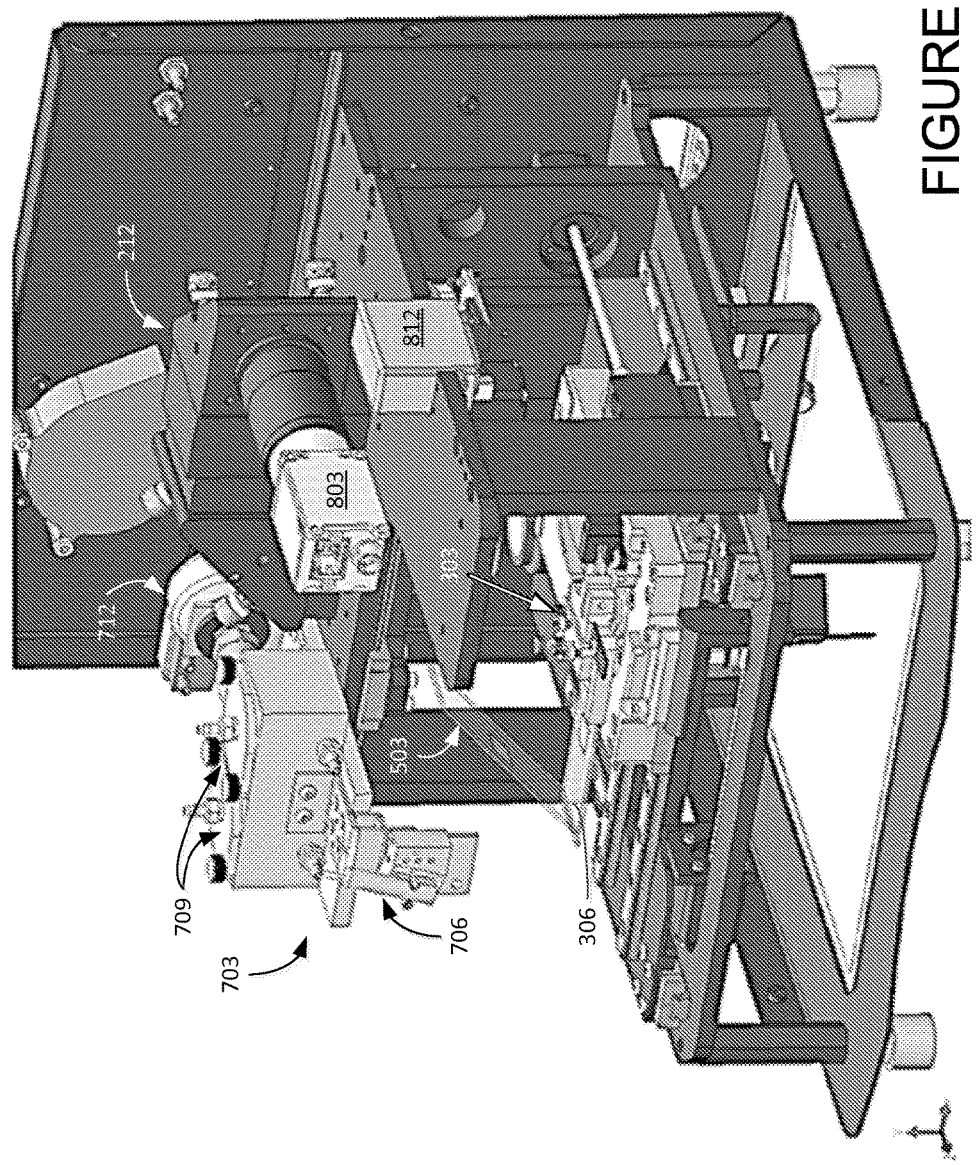

When the slide preparation is completed, the slide positioner 203 can retract and rotate the slide 306 under the digital microscope, as illustrated in FIGS. 3C and 3D, utilizing the light source 206, one or more microscopic lenses 209 and the image capture unit 212 for imaging. As shown in FIG. 5A, the light source 206 is positioned below the level of the sample slide 306 for illumination during imaging. Sufficient cooling is included to prevent distortion of the captured images by heat from the light source 206. A plurality of microscopic lenses 209 can be positioned above the level of the sample slide 306. One of the lenses 209 can be selected for imaging by the image capture unit 212 and linearly adjusted for focus on the sample. As can be seen in FIG. 5A, two or more microscopic lenses 209 can be mounted on a common baseplate 806, which is supported by a pair of guide rails 809. By moving the baseplate 806 along the guide rails 809, the desired lens magnification can be selected. A motor 812 (or solenoid) can be controlled to shift the baseplate 806 to align the appropriate lens 209 with the image capture unit 212. As depicted in FIG. 5C, linkage 815 can be used to translate the rotational motion of the motor 812 to the linear motion of the baseplate 806. Sensors and/or mechanical stops can be included to ensure proper alignment of the selected lens with the image capture unit 212. A dust shield can be provided over the back side of the lenses to avoid accumulation of dust or other dirt on the lenses 209.

With the selected microscopic lens 209 in position, the lens 209 and/or light source 206 can be adjusted for examination and imaging of the sample. For example, the selected lens 209 can be adjusted using a stepper or servo motor 818. Using appropriate gearing or thread pitch allows for very fine adjustment of the lens 209, which improves the ability to focus the image for capture. The location of the surface of the sample slide 306 can initially be determined by focusing on an etched portion of the slide 306. Focus of the microscopic lens 209 can then be automatically carried out by the slide processing unit 100 or manually carried out by the user of the slide processing unit 100. A hard stop can be provided to prevent the lens 206 from striking the sample slide 306 during adjustment.

With the treated sample under the digital microscope, it is possible to automatically identify a monolayer of the smeared sample. As the sample is smeared across the slide 306, the thickness of the sample on the slide 306 will decrease or be feathered out until the sample smearing is completed. Towards the end of the smearing, there is an area where a monolayer of cells exists (i.e., where the cells are one cell thick, nominally 3-5 microns). In some implementations, the location of the monolayer can be determined by measuring the light passing through the slide. Initially, light can be measured through the glass of the slide 306 on both sides of the sample where no sample exists. This allows the total amount of light coming through clear glass to be determined. The digital microscope can then search for an area where a predefined percentage of the total light is detected passing through the smeared sample. For example, when the light passing through an area of the smeared sample is about 57% of the total light through clear glass, then a monolayer exists in that area. In this way, the location of a monolayer can be determined in the smeared sample.

The slide processing unit 100 can be used to automatically acquire images of treated samples and transmit the images for storage and/or evaluation at a remote location. Images of the sample on the slide 306 can be digitized automatically in a mosaic fashion using the image capture unit 212, which includes mirrors, lenses, and/or the imaging device 803. The images may be initially acquired at a high resolution and stored in memory in the slide processing unit 100. The location (or relative position) of each of the mosaic images, the operating conditions of the light source 206, lens 209 and/or image capture unit 212, and/or identification of the sample slide 306 can also be stored in memory. In some implementations, the slide processing unit 100 can also send the acquired images for external storage in a local or remote data store. For example, the images can be transmitted to secure data store in the cloud. The slide processing unit 100 can be configured to send the images for external storage at the time of acquisition or store the images in the memory of the slide processing unit 100 at the time of acquisition and send them for external storage at a later time. For example, the images can be transmitted at a scheduled time (e.g., after normal business hours when usage of the network is low) or when the slide processing unit 100 is idle.

Figure 10:
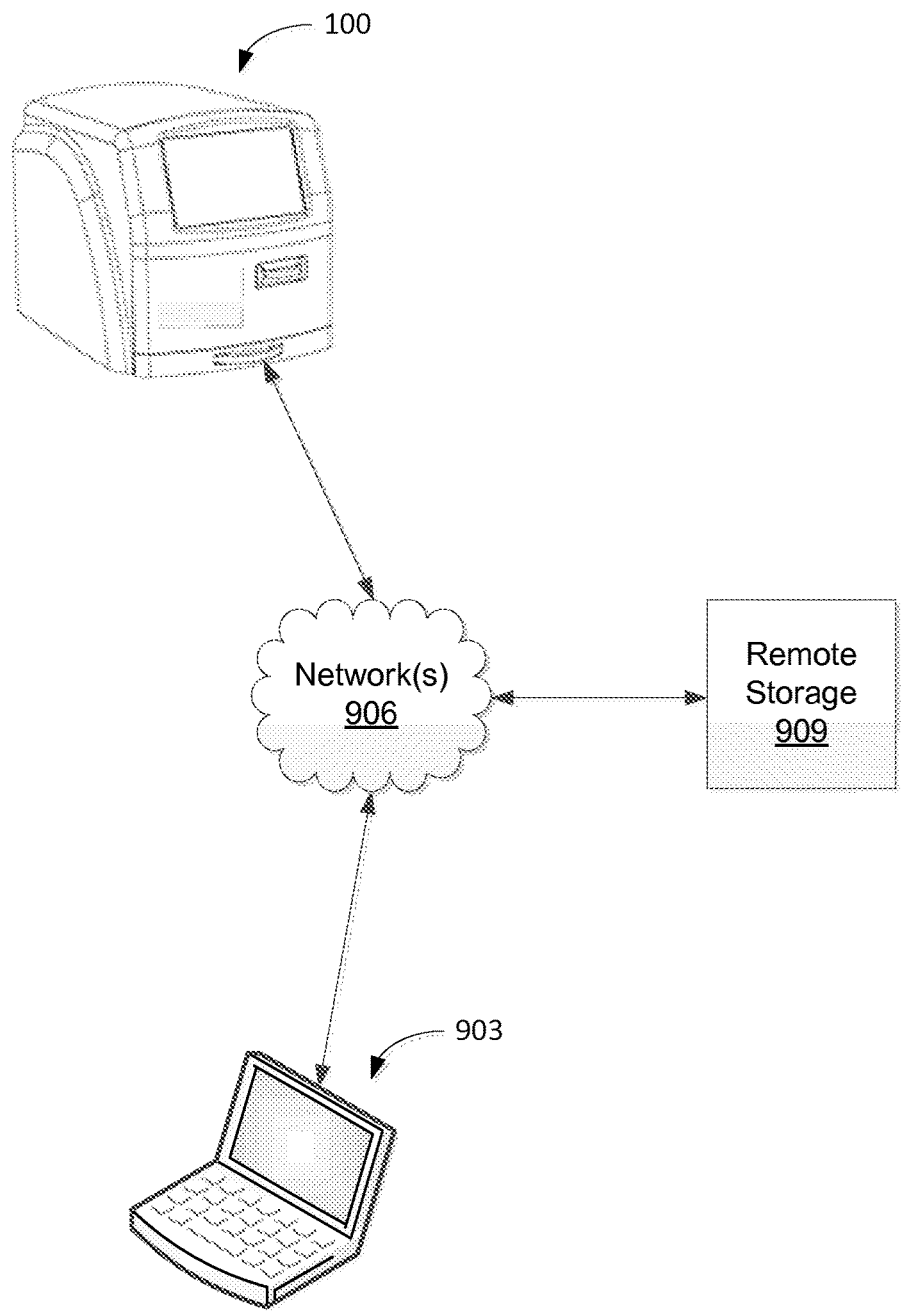
FIG. 10 is a graphical representation of a system for remote access and storage of slide processing using a slide processing unit of FIGS. 1 and 2 in accordance with various embodiments of the present disclosure.

The digitized images can be made visible to either the local operator on the display screen 103 (FIG. 1) and/or transmitted for review by others skilled in the art of pathology. FIG. 10 is a graphical representation illustrating a system for remotely accessing and/or controlling the slide processing unit 100. For example, communication can be established between the slide processing unit 100 and a user device 903 (e.g., a computer, tablet, smart phone, etc.) via a secure network connection over one or more networks 906 (e.g., an intranet, the Internet and/or a cellular network). As discussed, the slide processing unit 100 can store the image data in local memory (or storage) and/or can store the image data in remote storage 909 for later access. The remote storage may be representative of one or more data stores as can be appreciated.

In addition, the data can be transmitted to the user device 903 of examination and evaluation. The user device 903 is representative of a plurality of devices that may be coupled to the network 906. The user device 903 may comprise, for example, a processor-based system such as a computer system. Such a computer system may be embodied in the form of a desktop computer, a laptop computer, personal digital assistants, cellular telephones, smartphones, web pads, tablet computer systems, or other devices with like capability. The user device 903 can include a display such as, for example, a liquid crystal display (LCD) displays, gas plasma-based flat panel displays, organic light emitting diode (OLEO) displays, electrophoretic ink (E ink) displays. LCD projectors, or other types of display devices, etc.

To improve the data transmission and reduce latency, the resolution of the acquired images can be reduced and compressed prior to transmission to the user device 903. For example, the resolution of the acquired imaged may be reduced by a predefined amount (e.g., 10 to 1), which does not affect the image quality for review by the user, and sent to the user device 903 using an appropriate compression format (e.g., jpeg). If a higher resolution image is requested by the user during evaluation of the images, then the image processing unit 100 can communicate the higher resolution information to the user device 903 for evaluation.

Examination of the sample in the image processing unit 100 can also be actively controlled either locally through the display screen 103 (or other user interface) or remotely via a secure connection with the user device 903. For example, a pathologist or other user can initially examine the lower resolution images to determine if a condition or problem exists. If there is a question regarding the sample, the higher resolution images can be requested for further examination. In some cases, the higher resolution images of specific areas of the sample can be requested by the pathologist or user to reduce the amount of data being requested. It is also possible for the pathologist or user to actively control the imaging of the sample in real time. This can be especially beneficial if a feature of the sample was captured over multiple images.

In some implementations, the pathologist or user can actively control some of the features of the slide processing unit 100 from a remote location. For example, examination of the treated sample can be remotely controlled in real time over the secure connection with the user device 903. Images can be transmitted to the user device 903 while commands are sent through an interface on the user device 903 to actively control viewing of the images. The commands can allow the pathologist or user to control the examination of the different areas of the stored image data or, with the sample slide 306 in the image processing unit 100, to control the active imaging of the sample in the image processing unit 100. Images that have been stored in the remote storage 909 can also be accessed through the user device 903.

In some cases, the user can implement real time control of the slide processing unit 100 with real time images being streamed to the user device 930. Features such as, but not limited to, control of the iris of the light source 206, remove switching of microscopic lenses (or objectives) 209, and control of viewing area can be controlled by a remote operator. Linear adjustment of the lens and/or selection of different lenses can also be controlled remotely. For instance, the pathologist or user can pan between different areas or change the resolution (or magnification) of the image(s) to focus the examination as desired. The pathologist or user can also control the image processing unit 100 while images are being captured of the sample in real time. In this way, the pathologist can examine the sample as if the slide 306 were at his or her location.

After imaging and/or examination of the sample is complete, the sample slide 306 can be returned to the carriage 106 by the slide positioner 203. The user can then remove the sample slide 306 from the slide processing unit 100 for retention or disposal. For example, the user can open the carriage 106 and pull the sample slide 306 out of the grasp of the slide clamp 303. The processed sample slide 306 can be reinserted into the slide processing unit 100 for subsequent examination using the microscopic lenses 209 and image capture unit 212 (FIG. 3C). The alignment arm 303 of the slide clamp 303 and the guide shoulder 427, slide stop 430 and clamp stop 433 of the mounting plate 309 (FIGS. 4A-4F) allow for consistent positioning of the sample slide 306 during the subsequent imaging. The sample slide 306 can be repositioned by the slide processing unit 100 to return to a location of a previously acquired image for reexamination by a user. In other implementation, the sample slide 306 can be deposited in the bottom of the image processing unit 100 for subsequent removal and disposal. For example, the sample slide 306 may be released and deposited in a receptacle in the bottom of the slide processing unit 100.

Tissue samples may also be processed by the slide processing unit 100 in a similar fashion. Thin slices of tissue may be placed on a slide 306 and introduced to the slide processing unit 100. As smearing would not be needed, the sample slide 306 would progress through the staining process described earlier (e.g., desiccation and/or chemical treatment) and positioned under the microscope lens 209 for digitization and/or review. In some implementations, a lump section of tissue may be introduced into the slide processing unit 100 in an appropriate sample jar and frozen section preparation may be automatically accomplished. The lump section can be dehydrated by forced air and/or vacuum desiccation with heat. The tissue can then be sectioned using, e.g., a piezo electrically driven knife (or sharp edge) and the resultant thin sections automatically placed on a slide 306. The sample slide 306 would then progress through the treatment process (e.g., staining) described earlier and positioned under the microscope lens 209 for digitization and/or review.

Figure 11:
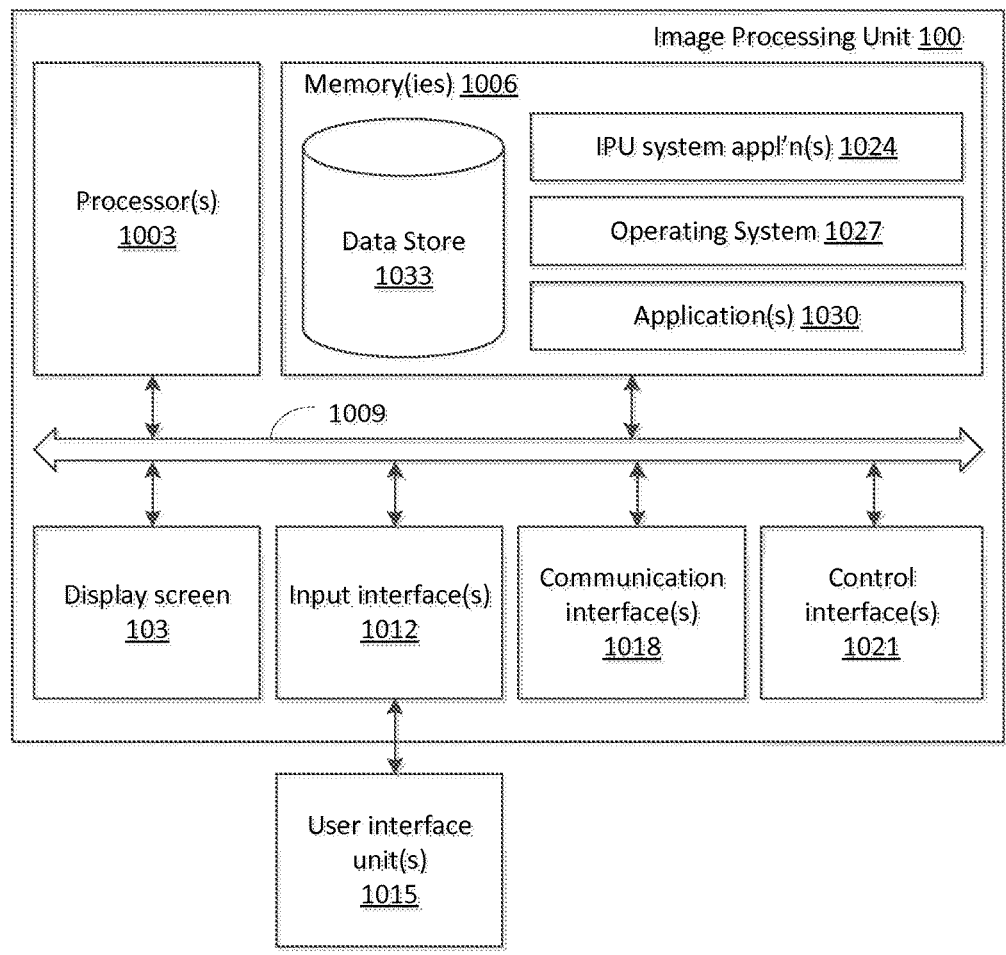
FIG. 11 is a schematic block diagram that illustrates an example of processing circuitry employed in the slide processing unit of FIGS. 1 and 2 in accordance with various embodiments of the present disclosure.

With reference now to FIG. 11, shown is a schematic block diagram of an example of processing circuitry that may be used to control the operation of the image processing unit 100 in accordance with various embodiments of the present disclosure. The processing circuitry includes at least one processor circuit, for example, having a processor 1003 and a memory 1006, both of which are coupled to a local interface 1009. To this end, the processing circuitry 1000 may be implemented using one or more circuits, one or more microprocessors, microcontrollers, application specific integrated circuits, dedicated hardware, digital signal processors, microcomputers, central processing units, field programmable gate arrays, programmable logic devices, state machines, or any combination thereof. The local interface 1009 may comprise, for example, a data bus with an accompanying address/control bus or other bus structure as can be appreciated. The processing circuitry 1000 can include a display screen 103 for rendering of generated graphics such as, e.g., a user interface and/or receive inputs from a user.

The processing circuitry 1000 can also include an input/output interface 1012 through which user input can be received from a user interface unit 1015 such, e.g., a keypad, mouse or touch screen and/or output from the image processing unit 100 can be sent to an external display for rendering. In addition, the processing circuitry 1000 can include one or more communication interfaces 1018 that allow the processing circuitry 1000 to communicatively couple with other communication devices or networks. The communication interfaces may include one or more wireless connection(s) such as, e.g., Bluetooth®, WiFi (e.g., 802.11) or other radio frequency (RF) connection and/or one or more wired connection(s). The processing circuitry 1000 can also include one or more control interface(s) 1021 in communication with motors (e.g., stepper or servo motors 321 and 330), solenoids, or other controllable devices used to control operation of the image processing unit 100.

Stored in the memory 1006 are both data and several components that are executable by the processor 1003. In particular, stored in the memory 1006 and executable by the processor 1003 are IPU (image processing unit) system application(s) 1024, an operating system 1027, and/or other applications 1030. IPU system applications 1024 can include applications that support, e.g., control of the operation of the image processing unit 100. For example, the IPU system applications 1024 can be configured to automatically process and acquire images of a sample on a slide 306 and provide capabilities for locally and remotely controlling the operation of the image processing unit 100 as has been described. It is understood that there may be other applications that are stored in the memory 1006 and are executable by the processor 1003 as can be appreciated. Where any component discussed herein is implemented in the form of software, any one of a number of programming languages may be employed such as, for example, C, C++, C#, Objective C, Java®, JavaScript®, Perl, PHP, Visual Basic®, Python®, Ruby, Deiphi®, Flash®, LabVIEW® or other programming languages. A data store 1033 and other data such as image data captured by the image capture unit 212 can also be stored in the memory 1006.

A number of software components are stored in the memory 1006 and are executable by the processor 1003. In this respect, the term "executable" means a program file that is in a form that can ultimately be run by the processor 1003. Examples of executable programs may be, for example, a compiled program that can be translated into machine code in a format that can be loaded into a random access portion of the memory 1006 and run by the processor 1003, source code that may be expressed in proper format such as object code that is capable of being loaded into a random access portion of the memory 1006 and executed by the processor 1003, or source code that may be interpreted by another executable program to generate instructions in a random access portion of the memory 1006 to be executed by the processor 1003, etc. An executable program may be stored in any portion or component of the memory 1006 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 1006 is defined herein as including both volatile and nonvolatile memory and data storage components. Volatile components are those that do not retain data values upon loss of power. Nonvolatile components are those that retain data upon a loss of power. Thus, the memory 1006 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor 1003 may represent multiple processors 1003 and the memory 1006 may represent multiple memories 1006 that operate in parallel processing circuits, respectively. In such a case, the local interface 1009 may be an appropriate network that facilitates communication between any two of the multiple processors 1003, between any processor 1003 and any of the memories 1006, or between any two of the memories 1006, etc. The local interface 1009 may comprise additional systems designed to coordinate this communication, including, for example, performing load balancing. The processor 1003 may be of electrical or of some other available construction.

Although the IPU system application(s) 1024, the operating system 1027, application(s) 1030, and other various systems described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, or other components, etc. Such technologies are generally well known by those skilled in the art and, consequently, are not described in detail herein.

Also any logic or application described herein, including the IPU system application(s) 1024 and/or application(s) 1030, that comprises software or code can be embodied in any non-transitory computer-readable medium for use by or in connection with an instruction execution system such as, for example, a processor 1003 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system. The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g 0.5%, 1.1%, 2.2%, 3.3%, and 4.4%)

within the indicated range. The term "about" can include traditional rounding according to significant figures of numerical values. In addition, the phrase "about 'x' to 'y'" includes "about 'x' to about 'y'".

Therefore, at least the following is claimed:

1. A system for processing microscope slides, comprising:
   a slide positioner configured to grip a proximal end of an individual slide supporting a fluid sample on an upper surface with a slide clamp, and to adjust positioning of the individual slide through linear and rotational motion of the slide clamp;
   a slide dispenser unit for dispensing smearing slides, the slide dispenser unit including a smearing slide magazine and a slide sled with a trough, where the smearing slide magazine is configured to eject one smearing slide of a stack of smearing slides into the trough of the slide sled, the trough configured to receive the one smearing slide ejected from the smearing slide magazine and allow the one smearing slide to slide down the trough of the slide sled onto the individual slide which is positioned beneath a distal end of the trough by the slide positioner, the slide sled comprising a structure adjacent to the distal end of the trough, the structure comprising a pivot point located over the one smearing slide as the one smearing slide rests on the individual slide positioned beneath the distal end of the trough, the pivot point allowing the one smearing slide to freely move and rock about a centerline extending along a length of the one smearing slide thereby allowing the one smearing slide to self-align an end of the one smearing slide with the upper surface of the individual slide such that a width of the one smearing slide rests evenly across a width of the individual slide, the one smearing slide supported by the slide sled at a predefined angle with respect to the upper surface of the individual slide with the end of the one smearing slide resting on the upper surface of the individual slide, where the slide positioner repositions the individual slide with respect to the end of the one smearing slide to smear the fluid sample along a length of the individual slide until the one smearing slide drops off a distal end of the individual slide allowing the one smearing slide to fall from the trough of the slide sled into a receptacle; and
   a slide treatment system for treating samples on slides, the slide treatment system including a jet nozzle coupled to a pressurized reservoir including a treatment fluid, the jet nozzle configured to dispense a micro stream of the treatment fluid at a targeted location on the fluid sample smeared on the individual slide after the slide positioner removes the individual slide from beneath the distal end of the trough and positions the individual slide beneath the jet nozzle.

2. The system of claim 1, further comprising an image capture unit configured to capture a digital image of at least a portion of the fluid sample smeared on the individual slide, the digital image captured via a lens when the slide positioner removes the individual slide from beneath the jet nozzle and positions the individual slide between the lens and a light source.

3. The system of claim 2, wherein the image capture unit comprises a CCD imaging device or a CMOS imaging device.

4. The system of claim 1, wherein the treatment fluid is a stain.

5. The system of claim 1, wherein the treatment fluid is methanol.

6. The system of claim 1, wherein the slide treatment system comprises a plurality of jet nozzles including the jet nozzle, the plurality of jet nozzles coupled to corresponding pressurized reservoirs including different treatment fluids, where individual jet nozzles of the plurality of jet nozzles are configured to dispense a micro stream of fluid from the corresponding pressurized reservoir at the targeted location on the fluid sample smeared on the individual slide when the individual slide is positioned below the plurality of jet nozzles, and the plurality of jet nozzles are configured to dispense the micro streams of fluid at the targeted location on the fluid sample smeared on the individual slide without additional movement of the individual slide.

7. The system of claim 1, wherein the slide positioner is further configured to reposition the individual slide beneath the jet nozzle to dispense another micro stream of the treatment fluid at a different targeted location on the fluid sample smeared on the individual slide.

8. The system of claim 1, wherein contact pressure of the one smearing slide on the upper surface of the individual slide with the fluid sample is provided by a weight of the one smearing slide.

9. The system of claim 1, wherein the slide positioner is configured to advance the individual slide under the end of the one smearing slide to contact the fluid sample, and retract the individual slide under the one smearing slide to smear the fluid sample along the length of the upper surface of the individual slide.

10. The system of claim 1, wherein the predefined angle is about 45degrees.

11. The system of claim 1, wherein the jet nozzle is electronically controlled to emit the micro stream as a pulsed burst of the treatment fluid.

12. A method for processing microscope slides, comprising:
    gripping a proximal end of an individual slide with a slide clamp of a slide positioner configured to adjust position of the individual slide through linear and rotational motion of the slide clamp, the individual slide including a sample disposed on a surface;
    positioning the individual slide below a slide dispenser unit using the slide positioner, the slide dispenser unit including a smearing slide magazine and a slide sled with a trough, where the smearing slide magazine is configured to eject one smearing slide of a stack of smearing slides into the trough of the slide sled, the trough configured to receive the one smearing slide elected from the smearing slide magazine and allow the one smearing slide to slide down the trough of the slide sled onto the surface of the individual slide which is positioned beneath a distal end of the trough by the slide positioner;
    dispensing the one smearing slide from the slide dispenser to contact the surface of the individual slide, the slide sled comprising a structure adjacent to the distal end of the trough, the structure comprising a pivot point located over the one smearing slide as the one smearing slide rests on the individual slide positioned beneath the distal end of the trough, the pivot point allowing the one smearing slide to freely move and rock about a centerline extending along a length of the one smearing slide thereby allowing the one smearing slide to self-align an end of the one smearing slide with the surface of the individual slide such that a width of the one smearing slide rests evenly across a width of the individual slide, the one smearing slide supported by the slide sled at a predefined angle with respect to the surface of the individual slide with the end of the one smearing slide resting on the surface of the individual slide;

advancing the individual slide under the end of the one smearing slide using the slide positioner to contact a lower edge of the one smearing slide with the sample on the individual slide;

retracting the individual slide under the end of the one smearing slide using the slide positioner, thereby smearing the sample along a length of the individual slide, where the slide positioner retracts the individual slide until the one smearing slide drops off a distal end of the individual slide allowing the one smearing slide to fall from the trough of the slide sled into a receptacle;

positioning the individual slide below a jet nozzle of a slide treatment system with the slide positioner, where the jet nozzle is coupled to a pressurized reservoir including a treatment fluid and the jet nozzle is configured to dispense a micro stream of the treatment fluid in a pulsed burst; and dispensing the micro stream of the treatment fluid onto the sample smeared on the individual slide using the jet nozzle, the micro stream of fluid dispensed at a targeted location on the sample smeared on the individual slide.

13. The method of claim 12, further comprising dispensing a micro stream of a second treatment fluid onto the sample using a second jet nozzle, the second treatment fluid dispensed onto the sample smeared on the individual slide at the targeted location without repositioning the individual slide.

14. The method of claim 12, further comprising:
repositioning the individual slide below to the jet nozzle; and
dispensing a second micro stream of the treatment fluid onto the sample at a different targeted location on the sample smeared on the individual slide using the jet nozzle.

15. The method of claim 12, wherein contact pressure of the one smearing slide with the individual slide is provided by a weight of the one smearing slide.

16. The method of claim 12, further comprising desiccating the sample smeared on the individual slide with air drawn across the individual slide by a vacuum.

17. The method of claim 12, further comprising:
repositioning the individual slide to an imaging location adjacent to a lens with the slide positioner; and
capturing an image of at least a portion of the sample smeared on the individual slide via the lens.

18. The method of claim 17, further comprising:
repositioning the individual slide to another imaging location adjacent to the lens with the slide positioner; and
capturing a second image of another portion of the sample smeared on the individual slide via the lens.

19. The method of claim 17, further comprising storing the image of the at least a portion of the sample smeared on the individual slide in memory.

20. The method of claim 17, further comprising communicating the image of the at least a portion of the sample smeared on the individual slide to a remote location via a network.

21. The method of claim 20, wherein the network is an Internet.

* * * * *